US008283890B2

(12) United States Patent
Videbaek

(10) Patent No.: US 8,283,890 B2
(45) Date of Patent: Oct. 9, 2012

(54) CHARGING STATION FOR BATTERY POWERED BIOPSY APPARATUS

(75) Inventor: Karsten Videbaek, Jyllinge (DK)

(73) Assignee: Bard Peripheral Vascular, Inc., Tempe, AZ (US)

(*) Notice: Subject to any disclaimer, the term of this patent is extended or adjusted under 35 U.S.C. 154(b) by 405 days.

(21) Appl. No.: 12/567,164

(22) Filed: Sep. 25, 2009

(65) Prior Publication Data
US 2011/0077551 A1 Mar. 31, 2011

(51) Int. Cl.
*H02J 7/00* (2006.01)
*A61B 10/00* (2006.01)
*A61B 17/32* (2006.01)

(52) U.S. Cl. ........ 320/115; 320/106; 320/107; 320/114; 320/132; 600/562; 600/564; 600/567; 600/568; 606/167; 606/170

(58) Field of Classification Search .................. 320/106, 320/107, 114, 115, 132; 600/562, 564, 567, 600/568; 606/167, 170
See application file for complete search history.

(56) References Cited

U.S. PATENT DOCUMENTS

| 737,293 | A | 8/1903 | Summerfeldt |
|---|---|---|---|
| 1,585,934 | A | 5/1926 | Muir |
| 1,663,761 | A | 3/1928 | Johnson |
| 2,953,934 | A | 9/1960 | Sundt |
| 3,019,733 | A | 2/1962 | Braid |
| 3,477,423 | A | 11/1969 | Griffith |
| 3,512,519 | A | 5/1970 | Hall |
| 3,561,429 | A | 2/1971 | Jewett et al. |
| 3,727,602 | A | 4/1973 | Hyden et al. |
| 3,732,858 | A | 5/1973 | Banko |
| 3,844,272 | A | 10/1974 | Banko |
| 4,282,884 | A | 8/1981 | Boebel |
| 4,354,092 | A | 10/1982 | Manabe et al. |
| 4,445,509 | A | 5/1984 | Auth |
| 4,577,629 | A | 3/1986 | Martinez |
| 4,589,414 | A | 5/1986 | Yoshida et al. |
| 4,603,694 | A | 8/1986 | Wheeler |
| 4,605,011 | A | 8/1986 | Naslund |
| 4,617,430 | A | 10/1986 | Bryant |
| 4,645,153 | A | 2/1987 | Granzow et al. |

(Continued)

FOREIGN PATENT DOCUMENTS
DE 3924291 A1 1/1991
(Continued)

OTHER PUBLICATIONS

MAXIM; Maxim8606; USB/AC Adapter, Li+ Linear Battery Charger with Integrated 50m Omega Battery Switch in TDFN; http://datasheets.maxim-ic.com/en/ds/MAX8606.pdf; Dec. 2008; Rev 1.

*Primary Examiner* — Sean Dougherty

(57) ABSTRACT

A charging station for a battery powered biopsy apparatus includes a charging dock having a housing and a charging unit contained in the housing. The charging unit has a set of electrical contacts. The housing is received in a first cavity of a driver assembly with the electrical contacts being coupled in electrical communication with the driver assembly when the driver assembly is mounted on the charging dock for charging. The charging unit provides a signal to the driver assembly to reset the driver assembly to an initialized state when the driver assembly is mounted to the charging station.

7 Claims, 21 Drawing Sheets

U.S. PATENT DOCUMENTS

| | | |
|---|---|---|
| 4,678,459 A | 7/1987 | Onik et al. |
| 4,696,298 A | 9/1987 | Higgins et al. |
| 4,702,260 A | 10/1987 | Wang |
| 4,850,354 A | 7/1989 | McGurk-Burleson et al. |
| 4,907,598 A | 3/1990 | Bauer |
| RE33,258 E | 7/1990 | Onik et al. |
| 4,952,817 A | 8/1990 | Bolan et al. |
| 4,986,807 A | 1/1991 | Farr |
| 4,989,614 A | 2/1991 | Dejter, Jr. et al. |
| 5,138,245 A | 8/1992 | Mattinger et al. |
| 5,146,921 A * | 9/1992 | Terwilliger et al. ........... 600/567 |
| 5,158,528 A | 10/1992 | Walker et al. |
| 5,176,628 A | 1/1993 | Charles et al. |
| 5,225,763 A | 7/1993 | Krohn et al. |
| 5,234,000 A | 8/1993 | Hakky et al. |
| 5,236,334 A | 8/1993 | Bennett |
| 5,249,583 A * | 10/1993 | Mallaby ....................... 600/567 |
| 5,282,477 A | 2/1994 | Bauer |
| 5,334,183 A | 8/1994 | Wuchinich |
| 5,439,474 A | 8/1995 | Li |
| 5,479,486 A | 12/1995 | Saji |
| 5,485,917 A | 1/1996 | Early |
| 5,492,130 A | 2/1996 | Chiou |
| 5,496,860 A | 3/1996 | Matsumoto et al. |
| 5,511,556 A | 4/1996 | DeSantis |
| 5,526,822 A | 6/1996 | Burbank et al. |
| 5,535,755 A | 7/1996 | Heske |
| 5,554,151 A | 9/1996 | Hinchliffe |
| 5,560,373 A | 10/1996 | DeSantis |
| 5,569,284 A | 10/1996 | Young et al. |
| 5,601,585 A | 2/1997 | Banik et al. |
| 5,602,449 A | 2/1997 | Krause et al. |
| 5,655,657 A | 8/1997 | Roshdy |
| 5,665,101 A | 9/1997 | Becker et al. |
| 5,669,394 A * | 9/1997 | Bergey et al. ................ 600/563 |
| 5,699,909 A | 12/1997 | Foster |
| 5,720,760 A | 2/1998 | Becker et al. |
| 5,735,264 A | 4/1998 | Siczek et al. |
| 5,755,714 A | 5/1998 | Murphy-Chutorian |
| 5,769,086 A | 6/1998 | Ritchart et al. |
| 5,775,333 A | 7/1998 | Burbank et al. |
| 5,792,167 A | 8/1998 | Kablik et al. |
| 5,827,305 A | 10/1998 | Gordon |
| 5,830,219 A | 11/1998 | Bird et al. |
| 5,908,233 A | 6/1999 | Heskett et al. |
| 5,916,229 A | 6/1999 | Evans |
| 5,928,164 A | 7/1999 | Burbank et al. |
| 5,944,673 A | 8/1999 | Gregorie et al. |
| 5,951,575 A | 9/1999 | Bolduc et al. |
| 5,964,716 A | 10/1999 | Gregorie et al. |
| D416,536 S | 11/1999 | Ross et al. |
| 5,976,164 A | 11/1999 | Bencini et al. |
| 5,980,469 A | 11/1999 | Burbank et al. |
| 6,007,556 A | 12/1999 | Kablik et al. |
| 6,017,316 A | 1/2000 | Ritchart et al. |
| 6,018,227 A | 1/2000 | Kumar et al. |
| 6,019,733 A | 2/2000 | Farascioni |
| 6,022,324 A | 2/2000 | Skinner |
| 6,022,325 A | 2/2000 | Siczek et al. |
| 6,050,955 A | 4/2000 | Bryan et al. |
| 6,086,544 A | 7/2000 | Hibner et al. |
| 6,120,462 A | 9/2000 | Hibner et al. |
| 6,142,955 A | 11/2000 | Farascioni et al. |
| 6,162,187 A | 12/2000 | Buzzard et al. |
| 6,193,673 B1 | 2/2001 | Viola et al. |
| 6,273,862 B1 | 8/2001 | Privitera et al. |
| 6,331,166 B1 | 12/2001 | Burbank et al. |
| 6,358,217 B1 | 3/2002 | Bourassa |
| 6,402,701 B1 | 6/2002 | Kaplan et al. |
| 6,419,641 B1 | 7/2002 | Mark et al. |
| 6,428,486 B2 | 8/2002 | Ritchart et al. |
| 6,428,487 B1 | 8/2002 | Burdorff et al. |
| 6,432,064 B1 | 8/2002 | Hibner et al. |
| 6,482,158 B2 | 11/2002 | Mault |
| 6,485,436 B1 | 11/2002 | Truckai et al. |
| 6,488,636 B2 | 12/2002 | Bryan et al. |
| 6,527,736 B1 | 3/2003 | Attinger et al. |
| 6,540,761 B2 | 4/2003 | Houser |
| 6,585,664 B2 | 7/2003 | Burdorff et al. |
| 6,638,235 B2 | 10/2003 | Miller et al. |
| D483,016 S | 12/2003 | Ma et al. |
| 6,659,105 B2 | 12/2003 | Burbank et al. |
| 6,659,338 B1 | 12/2003 | Dittmann et al. |
| 6,683,439 B2 | 1/2004 | Takano et al. |
| 6,689,072 B2 | 2/2004 | Kaplan et al. |
| 6,695,786 B2 | 2/2004 | Wang et al. |
| 6,712,774 B2 | 3/2004 | Voegele et al. |
| D489,322 S | 5/2004 | Sawai et al. |
| 6,752,768 B2 | 6/2004 | Burdorff et al. |
| 6,753,671 B1 | 6/2004 | Harvey |
| 6,758,824 B1 | 7/2004 | Miller et al. |
| 6,764,495 B2 | 7/2004 | Lee et al. |
| D493,801 S | 8/2004 | Byun |
| 6,832,990 B2 | 12/2004 | Kortenbach et al. |
| 6,849,080 B2 | 2/2005 | Lee et al. |
| D508,458 S | 8/2005 | Solland et al. |
| 6,926,676 B2 | 8/2005 | Turturro et al. |
| D525,583 S | 7/2006 | Vu |
| 7,153,274 B2 | 12/2006 | Stephens et al. |
| 7,189,206 B2 | 3/2007 | Quick et al. |
| 7,219,867 B2 | 5/2007 | Kalis et al. |
| 7,226,424 B2 | 6/2007 | Ritchart et al. |
| 7,276,032 B2 | 10/2007 | Hibner |
| D559,485 S | 1/2008 | Fjellman |
| 7,328,794 B2 | 2/2008 | Lubs et al. |
| 7,347,829 B2 | 3/2008 | Mark et al. |
| D568,327 S | 5/2008 | Fitch et al. |
| D568,808 S | 5/2008 | Hamasaki |
| 7,374,544 B2 | 5/2008 | Freeman et al. |
| D572,188 S | 7/2008 | Prat-Pfister |
| 7,397,654 B2 | 7/2008 | Mori |
| 7,402,140 B2 | 7/2008 | Spero et al. |
| 7,405,536 B2 | 7/2008 | Watts |
| 7,407,054 B2 | 8/2008 | Seiler et al. |
| 7,432,813 B2 | 10/2008 | Postma |
| 7,464,040 B2 | 12/2008 | Joao |
| 7,490,048 B2 | 2/2009 | Joao |
| D590,834 S | 4/2009 | Richter |
| 7,517,321 B2 | 4/2009 | McCullough et al. |
| D593,103 S | 5/2009 | Richter |
| D593,566 S | 6/2009 | Richter |
| D595,722 S | 7/2009 | Miyawaki |
| 7,648,466 B2 | 1/2010 | Stephens et al. |
| 7,883,476 B2 | 2/2011 | Miller et al. |
| 2001/0007925 A1 | 7/2001 | Ritchart et al. |
| 2001/0011156 A1 | 8/2001 | Viola et al. |
| 2001/0034530 A1 | 10/2001 | Malackowski et al. |
| 2001/0047183 A1 | 11/2001 | Privitera et al. |
| 2002/0065474 A1 | 5/2002 | Viola |
| 2002/0067151 A1 | 6/2002 | Tanishita |
| 2002/0082518 A1 | 6/2002 | Weiss et al. |
| 2002/0107043 A1 | 8/2002 | Adamson et al. |
| 2002/0120212 A1 | 8/2002 | Ritchart et al. |
| 2003/0130677 A1 | 7/2003 | Whitman et al. |
| 2003/0163142 A1 | 8/2003 | Paltieli et al. |
| 2004/0015079 A1 | 1/2004 | Berger et al. |
| 2004/0019297 A1 | 1/2004 | Angel |
| 2004/0049128 A1 | 3/2004 | Miller et al. |
| 2004/0092992 A1 | 5/2004 | Adams et al. |
| 2004/0215079 A1 | 10/2004 | Mueller, Jr. et al. |
| 2004/0220495 A1 * | 11/2004 | Cahir et al. ................... 600/562 |
| 2004/0267157 A1 | 12/2004 | Miller et al. |
| 2005/0004559 A1 | 1/2005 | Quick et al. |
| 2005/0020909 A1 | 1/2005 | Moctezuma de la Barrera et al. |
| 2005/0027210 A1 | 2/2005 | Miller |
| 2005/0049489 A1 | 3/2005 | Foerster et al. |
| 2005/0049521 A1 | 3/2005 | Miller et al. |
| 2005/0080355 A1 | 4/2005 | Mark |
| 2005/0113715 A1 | 5/2005 | Schwindt et al. |
| 2005/0113716 A1 | 5/2005 | Mueller, Jr. et al. |
| 2005/0124915 A1 | 6/2005 | Eggers et al. |
| 2005/0165328 A1 | 7/2005 | Heske et al. |
| 2005/0193451 A1 | 9/2005 | Quistgaard et al. |
| 2005/0203439 A1 | 9/2005 | Heske et al. |
| 2005/0209530 A1 | 9/2005 | Pflueger |
| 2005/0275378 A1 | 12/2005 | Canino et al. |
| 2005/0277829 A1 | 12/2005 | Tsonton et al. |

| | | |
|---|---|---|
| 2006/0030784 A1 | 2/2006 | Miller et al. |
| 2006/0113958 A1 | 6/2006 | Lobert et al. |
| 2006/0116603 A1 | 6/2006 | Shibazaki et al. |
| 2006/0129063 A1 | 6/2006 | Thompson et al. |
| 2006/0173377 A1 | 8/2006 | McCullough et al. |
| 2006/0184063 A1 | 8/2006 | Miller |
| 2006/0241515 A1 | 10/2006 | Jones et al. |
| 2006/0258956 A1 | 11/2006 | Haberstich et al. |
| 2007/0016101 A1 | 1/2007 | Feldman et al. |
| 2007/0027407 A1 | 2/2007 | Miller |
| 2007/0073326 A1 | 3/2007 | Miller et al. |
| 2007/0090788 A1 | 4/2007 | Hansford et al. |
| 2007/0118049 A1 | 5/2007 | Viola |
| 2007/0149893 A1* | 6/2007 | Heske et al. .............. 600/566 |
| 2007/0149894 A1 | 6/2007 | Heske et al. |
| 2007/0161925 A1 | 7/2007 | Quick et al. |
| 2007/0167782 A1 | 7/2007 | Callahan et al. |
| 2007/0213590 A1 | 9/2007 | Squicciarini |
| 2007/0213630 A1 | 9/2007 | Beckman et al. |
| 2007/0213632 A1 | 9/2007 | Okazaki et al. |
| 2007/0219572 A1 | 9/2007 | Deck et al. |
| 2007/0236180 A1 | 10/2007 | Rodgers |
| 2007/0239067 A1 | 10/2007 | Hibner et al. |
| 2007/0255173 A1 | 11/2007 | Hibner |
| 2007/0276288 A1 | 11/2007 | Khaw |
| 2007/0287933 A1 | 12/2007 | Phan et al. |
| 2007/0293788 A1 | 12/2007 | Entrekin et al. |
| 2008/0004545 A1 | 1/2008 | Garrison |
| 2008/0007217 A1 | 1/2008 | Riley |
| 2008/0015429 A1 | 1/2008 | Tsonton et al. |
| 2008/0021487 A1 | 1/2008 | Heisler |
| 2008/0021488 A1 | 1/2008 | Berberich |
| 2008/0030170 A1 | 2/2008 | Dacquay et al. |
| 2008/0064925 A1 | 3/2008 | Gill et al. |
| 2008/0064984 A1 | 3/2008 | Pflueger |
| 2008/0071193 A1 | 3/2008 | Reuber et al. |
| 2008/0079391 A1 | 4/2008 | Schroeck et al. |
| 2008/0110261 A1 | 5/2008 | Randall et al. |
| 2008/0135443 A1 | 6/2008 | Frojd et al. |
| 2008/0146962 A1 | 6/2008 | Ritchie et al. |
| 2008/0146965 A1 | 6/2008 | Privitera et al. |
| 2008/0154151 A1 | 6/2008 | Ritchart et al. |
| 2008/0161682 A1 | 7/2008 | Kendrick et al. |
| 2008/0161718 A1 | 7/2008 | Schwindt |
| 2008/0161720 A1 | 7/2008 | Nicoson et al. |
| 2008/0183099 A1 | 7/2008 | Jorgensen et al. |
| 2008/0195066 A1 | 8/2008 | Speeg et al. |
| 2008/0200833 A1 | 8/2008 | Hardin et al. |
| 2008/0200836 A1 | 8/2008 | Speeg et al. |
| 2008/0208194 A1 | 8/2008 | Bickenbach |
| 2008/0215056 A1 | 9/2008 | Miller et al. |
| 2008/0221443 A1 | 9/2008 | Ritchie et al. |
| 2008/0221444 A1 | 9/2008 | Ritchie et al. |
| 2008/0221478 A1 | 9/2008 | Ritchie et al. |
| 2008/0221479 A1 | 9/2008 | Ritchie et al. |
| 2008/0221480 A1 | 9/2008 | Hibner et al. |
| 2008/0228104 A1 | 9/2008 | Uber et al. |
| 2008/0232604 A1 | 9/2008 | Dufresne et al. |
| 2008/0234715 A1 | 9/2008 | Pesce et al. |
| 2008/0281225 A1 | 11/2008 | Spero et al. |
| 2008/0287826 A1 | 11/2008 | Videbaek et al. |
| 2008/0306406 A1 | 12/2008 | Thompson et al. |
| 2008/0308607 A1 | 12/2008 | Timm et al. |
| 2008/0319341 A1 | 12/2008 | Taylor et al. |
| 2009/0030405 A1 | 1/2009 | Quick et al. |
| 2009/0062624 A1 | 3/2009 | Neville |
| 2009/0082695 A1 | 3/2009 | Whitehead |
| 2009/0125062 A1 | 5/2009 | Arnin |
| 2009/0137927 A1 | 5/2009 | Miller |
| 2009/0171243 A1* | 7/2009 | Hibner et al. .............. 600/566 |
| 2009/0227893 A1 | 9/2009 | Coonahan et al. |
| 2010/0030020 A1* | 2/2010 | Sanders et al. .............. 600/109 |
| 2010/0106053 A1 | 4/2010 | Videbaek et al. |
| 2010/0210966 A1 | 8/2010 | Videbaek |
| 2010/0292607 A1 | 11/2010 | Moore et al. |
| 2010/0317995 A1* | 12/2010 | Hibner et al. .............. 600/564 |
| 2010/0317997 A1* | 12/2010 | Hibner et al. .............. 600/567 |
| 2010/0317998 A1* | 12/2010 | Hibner et al. .............. 600/567 |
| 2011/0054350 A1 | 3/2011 | Videbaek |
| 2011/0087131 A1 | 4/2011 | Videbaek |
| 2011/0105945 A1 | 5/2011 | Videbaek et al. |
| 2011/0105946 A1 | 5/2011 | Sorensen et al. |

FOREIGN PATENT DOCUMENTS

| | | |
|---|---|---|
| DE | 10026303 A1 | 2/2002 |
| DE | 10235480 A1 | 2/2004 |
| EP | 0995400 A1 | 4/2000 |
| EP | 1520518 A2 | 4/2005 |
| EP | 2095772 A1 | 9/2009 |
| FR | 1345429 A | 12/1963 |
| FR | 2739293 A1 | 4/1997 |
| GB | 2018601 A | 10/1979 |
| JP | H10508504 A | 8/1998 |
| JP | 2005530554 A | 10/2005 |
| JP | 2006509545 A | 3/2006 |
| JP | 2006528907 A | 12/2006 |
| JP | 2007502159 A | 2/2007 |
| WO | 9624289 A2 | 8/1996 |
| WO | 9835615 A1 | 8/1998 |
| WO | 9846290 A1 | 10/1998 |
| WO | 9933501 A1 | 7/1999 |
| WO | 0004832 A1 | 2/2000 |
| WO | 0222023 A1 | 3/2002 |
| WO | 02069808 A2 | 9/2002 |
| WO | 2006015302 A1 | 2/2006 |
| WO | 2007047128 A1 | 4/2007 |
| WO | 2007112751 A2 | 10/2007 |
| WO | 2008021687 A1 | 2/2008 |
| WO | 2008024684 A2 | 2/2008 |
| WO | 2008040812 A1 | 4/2008 |
| WO | 2008131362 A2 | 10/2008 |
| WO | 2011019343 A1 | 2/2011 |

* cited by examiner

CHARGING STATION FOR BATTERY POWERED BIOPSY APPARATUS

CROSS-REFERENCE TO RELATED APPLICATIONS

This application is related to International Application No. PCT/US2009/040663, filed Apr. 15, 2009, and U.S. patent application Ser. No. 12/551,819 filed Sep. 1, 2009.

MICROFICHE APPENDIX

None.

GOVERNMENT RIGHTS IN PATENT

None.

BACKGROUND OF THE INVENTION

1. Field of the Invention

The present invention relates to a biopsy apparatus, and, more particularly, to a charging station for a battery powered biopsy apparatus.

2. Description of the Related Art

A biopsy may be performed on a patient to help in determining whether the cells in a biopsied region are cancerous. One type of vacuum assisted biopsy apparatus includes a hand-held driver assembly having a vacuum source, and a disposable biopsy probe assembly configured for releasable attachment to the driver assembly. One biopsy technique used to evaluate breast tissue, for example, involves inserting a biopsy probe into the breast tissue region of interest to capture one or more tissue samples from the region.

The biopsy probe typically includes a biopsy cannula, e.g., a needle, having a cylindrical side wall defining a lumen, and having a side sample notch located near the distal end that extends though the side wall to the lumen. A cutting cannula is positioned coaxial with the biopsy cannula to selectively open and close the sample notch. Vacuum is applied to the lumen, and in turn to the sample notch, for receiving the tissue to be sampled when the sample notch is opened, after which the sample notch is closed by the cutting cannula to sever the tissue, and the severed tissue is transported by vacuum out of the lumen and collected.

One type of hand-held driver assembly is battery powered, which requires occasional charging to keep the biopsy apparatus operational.

SUMMARY OF THE INVENTION

The present invention provides a charging station for a battery powered biopsy apparatus.

As used herein, the terms "first" and "second" preceding an element name, e.g., first housing, second housing, third housing, etc., are for identification purposes to distinguish between different elements having similar characteristic, and are not intended to necessarily imply order, unless otherwise specified, nor are the terms "first" and "second" intended to preclude the inclusion of additional similar elements.

The invention, in one form thereof, is directed to a charging station for a battery powered biopsy apparatus. The biopsy apparatus includes a driver assembly configured for releasable attachment to a biopsy probe assembly. The driver assembly has a battery and a first housing configured to be grasped by a user. The first housing has a first cavity. The first cavity of the driver assembly is configured for receiving a second housing of the biopsy probe assembly when the biopsy probe assembly is mounted to the driver assembly. The second housing has a first shape. The charging station includes a charging dock having a third housing and a charging unit contained in the third housing. The charging unit has a set of electrical contacts. The third housing has a second shape. The third housing is received in the first cavity of the driver assembly with the electrical contacts being coupled in electrical communication with the driver assembly when the driver assembly is mounted on the charging dock for charging. The charging unit provides a signal to the driver assembly to reset the driver assembly to an initialized state when the driver assembly is mounted to the charging station.

The invention, in another form thereof, is directed to a biopsy system, including a driver assembly, a biopsy probe assembly, and a charging dock. The driver assembly has an electromechanical power source with a battery and has a first housing configured to be grasped by a user. The first housing has a first cavity. The biopsy probe assembly is configured for releasable attachment to the driver assembly. The biopsy probe assembly has a frame, a biopsy probe, a transmission device and a second housing. The biopsy probe and the second housing are mounted to the frame. The second housing contains at least a portion of the transmission device with the biopsy probe being drivably coupled to the transmission device. The transmission device is configured for releasable driven coupling to the electromechanical power source of the driver assembly. The first cavity of the driver assembly is configured for receiving the second housing of the biopsy probe assembly when the driver assembly is mounted to the biopsy probe assembly. The second housing has a first shape. The charging dock has a third housing and a charging unit contained in the third housing. The charging unit has a set of electrical contacts. The third housing has a second shape substantially the same as the first shape of the second housing of the biopsy probe assembly. The third housing is received in the first cavity of the driver assembly with the electrical contacts being coupled in electrical communication with the driver assembly when the driver assembly is mounted on the charging dock for charging.

The invention, in another form thereof, is directed to a method for charging a battery operated biopsy apparatus. The method includes providing a signal to a driver assembly of the battery operated biopsy apparatus indicating that a connection between first electrical contacts of a charging unit of a charging station and second electrical contacts of the driver assembly has been made; upon receiving the signal, determining whether the driver assembly is in an error state, wherein if the error state exists, then resetting the driver assembly to an initialized state; and charging a battery of the driver assembly.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplifications set out herein illustrate an embodiment of the invention, and such exemplifications are not to be construed as limiting the scope of the invention in any manner.

DETAILED DESCRIPTION OF THE INVENTION

Figure 1:
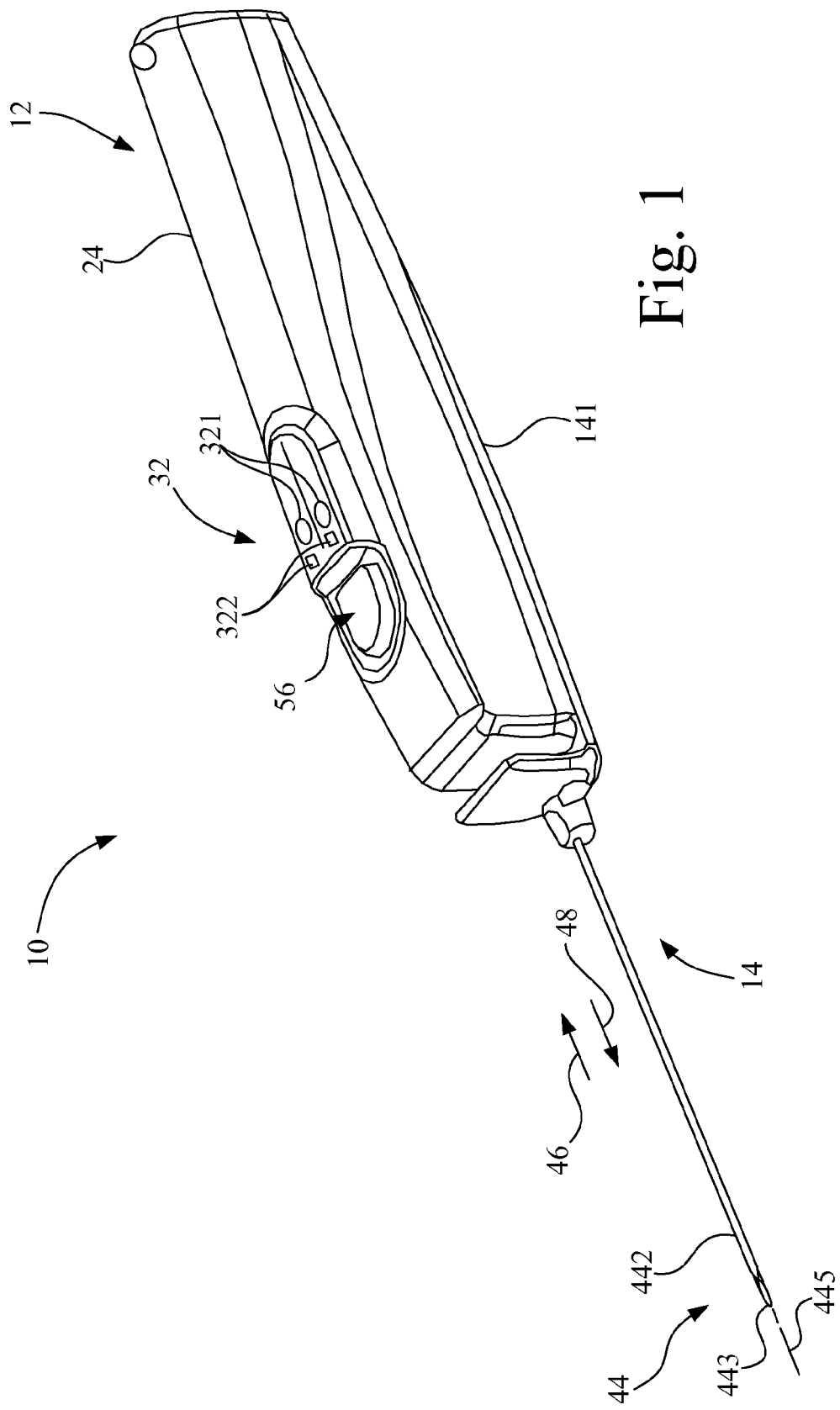
FIG. 1 is a perspective view of a biopsy apparatus, configured in accordance with an embodiment of the present invention, with a disposable biopsy probe mounted to a driver assembly.
Figure 2:
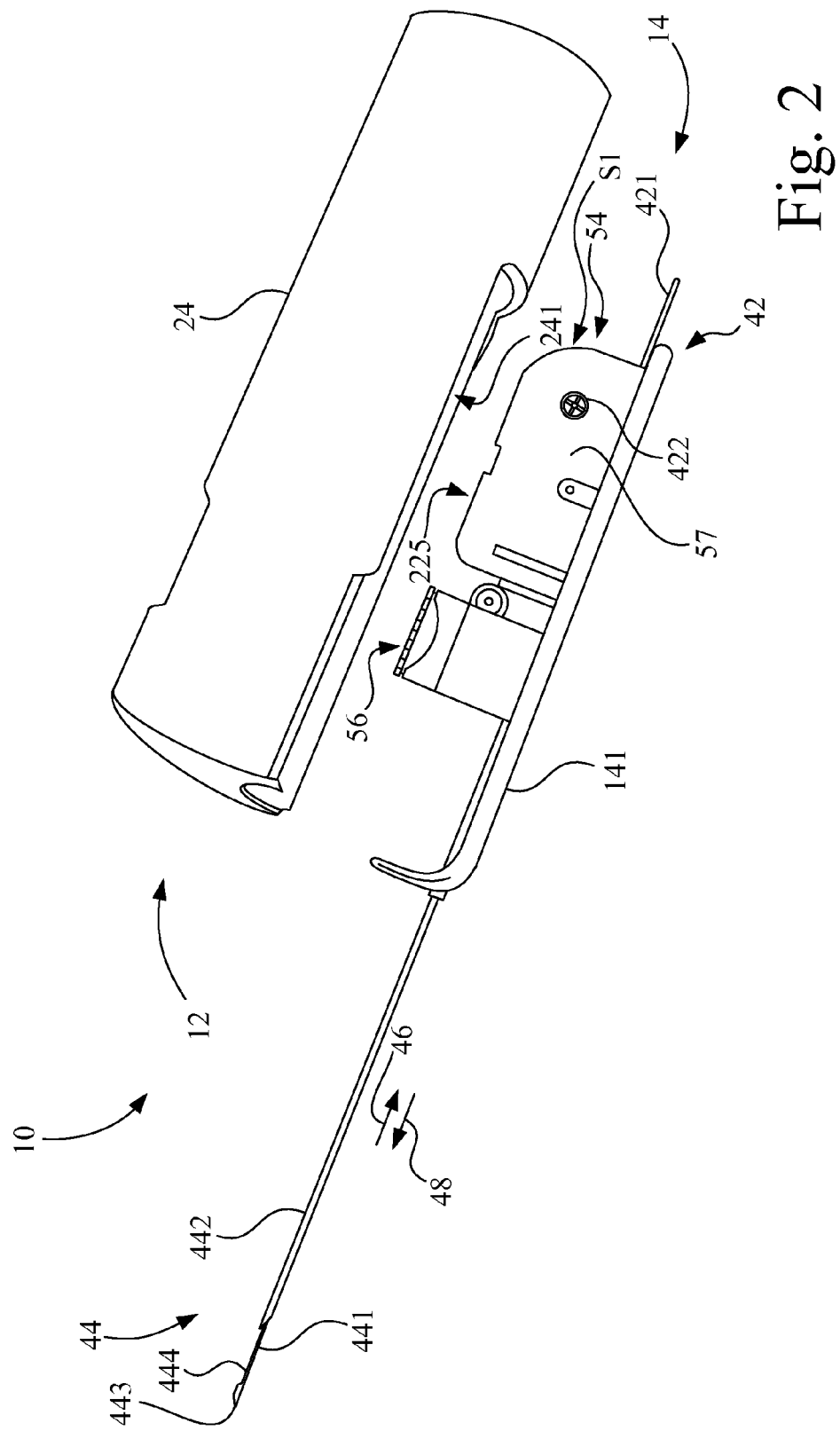
FIG. 2 is a perspective view of a biopsy apparatus of FIG. 1, with the disposable biopsy probe detached from the driver assembly.

Referring now to the drawings, and more particularly to FIGS. 1 and 2, there is shown a biopsy apparatus 10 which generally includes a non-invasive, e.g., non-disposable, driver assembly 12 and a disposable biopsy probe assembly 14.

Figure 3:
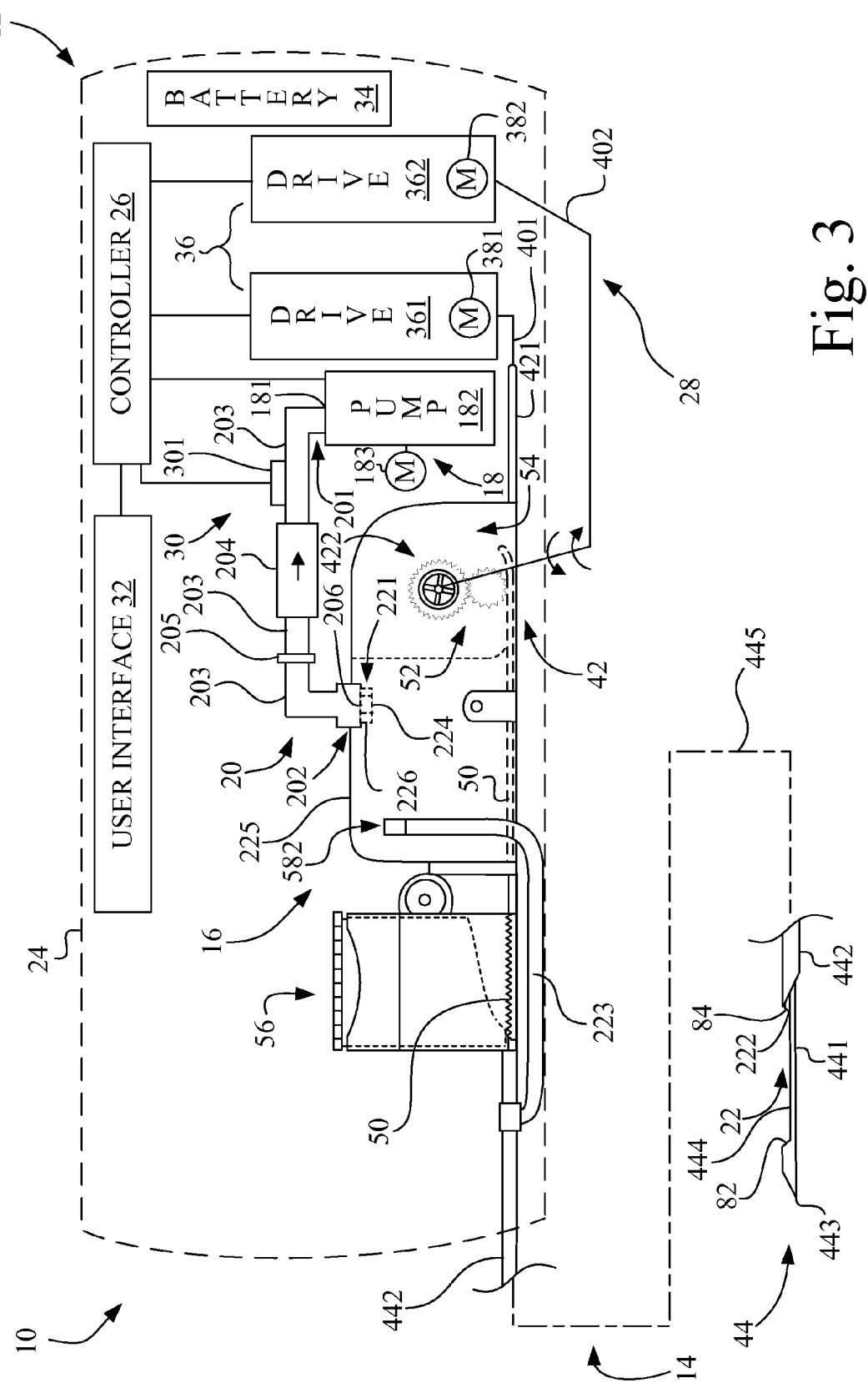
FIG. 3 is a schematic representation of the biopsy apparatus of FIG. 1.

Referring also to FIG. 3, driver assembly 12 and disposable biopsy probe assembly 14 collectively include a fluid management system 16 that includes a vacuum source 18, first vacuum path 20 and a second vacuum path 22. Vacuum source 18 and a first vacuum path 20 are permanently associated with driver assembly 12, and a second vacuum path 22 is permanently associated with disposable biopsy probe assembly 14, as more fully described below, to help facilitate the safe and effective collection of a biopsy tissue sample.

As used herein, the term "non-disposable" is used to refer to a device that is intended for use on multiple patients during the lifetime of the device, and the term "disposable" is used to refer to a device that is intended to be disposed of after use on a single patient. Also, the term "vacuum path" means a fluid passageway used to facilitate a vacuum between two points, the fluid passageway passing through one or more components, such as for example, one or more of tubing, conduits, couplers, and interposed devices. Also, the term "permanently associated" means a connection that is not intended for releasable attachment on a routine basis during the lifetime of the components. Thus, for example, driver assembly 12 including vacuum source 18 and first vacuum path 20 is reusable as a unit in its entirety, whereas disposable biopsy probe assembly 14 and second vacuum path 22 are disposable as a unit in its entirety.

Driver assembly 12 includes a housing 24 configured, and ergonomically designed, to be grasped by a user. Driver assembly 12 includes (contained within housing 24) vacuum source 18, first vacuum path 20, a controller 26, an electromechanical power source 28, and a vacuum monitoring mechanism 30. A user interface 32 is located to be mounted to, and externally accessible with respect to, housing 24. Housing 24 defines an elongate cavity 241 which is configured for receiving a corresponding housing 57 of biopsy probe assembly 14 when driver assembly 12 is mounted to biopsy probe assembly 14.

Controller 26 is communicatively coupled to electromechanical power source 28, vacuum source 18, user interface 32, and vacuum monitoring mechanism 30. Controller 26 may include, for example, a microprocessor and associated memory for executing program instructions to perform functions associated with the retrieval of biopsy tissue samples, such as controlling one or more components of vacuum source 18 and electromechanical power source 28. Controller 26 also may execute program instructions to monitor one or more conditions and/or positions of components of biopsy apparatus 10, and to monitor the status of fluid management system 16 associated with driver assembly 12 and biopsy probe assembly 14.

The user interface 32 includes control buttons 321 and visual indicators 322, with control buttons 321 providing user control over various functions of biopsy apparatus 10, and visual indicators 322 providing visual feedback of the status of one or more conditions and/or positions of components of biopsy apparatus 10.

The electromechanical power source 28 may include, for example, an electrical energy source, e.g., battery, 34 and an electrical drive assembly 36. Battery 34 may be, for example, a rechargeable battery. Battery 34 provides electrical power to all electrically powered components in biopsy apparatus 10, and thus for simplicity in the drawings, such electrical couplings are not shown. For example, battery 34 is electrically coupled to vacuum source 18, controller 26, user interface 32 and electrical drive assembly 36.

In the present embodiment, electrical drive assembly 36 includes a first drive 361 and a second drive 362, each being respectively coupled to battery 34, and each of first drive 361 and second drive 362 respectively electrically and controllably coupled to user interface 32.

First drive 361 may include an electrical motor 381 and a motion transfer unit 401 (shown schematically by a line). Second drive 362 may include an electrical motor 382 and a motion transfer unit 402 (shown schematically by a line). Each electrical motor 381, 382 may be, for example, a direct current (DC) motor, stepper motor, etc. Motion transfer unit 401 of first drive 361 may be configured, for example, with a rotational-to-linear motion converter, such as a worm gear arrangement, rack and pinion arrangement, solenoid-slide arrangement, etc. Motion transfer unit 402 of second drive 362 may be configured to transmit rotary motion. Each of first drive 361 and second drive 362 may include one or more of a gear, gear train, belt/pulley arrangement, etc.

Vacuum source 18 is electrically coupled to battery 34, and has a vacuum source port 181 for establishing a vacuum. Vacuum source 18 is electrically and controllably coupled to user interface 32. Vacuum source 18 may further include, for example, a vacuum pump 182 driven by an electric motor 183. Vacuum pump 182 may be, for example, a peristaltic pump, a diaphragm pump, syringe-type pump, etc.

Figure 4A:
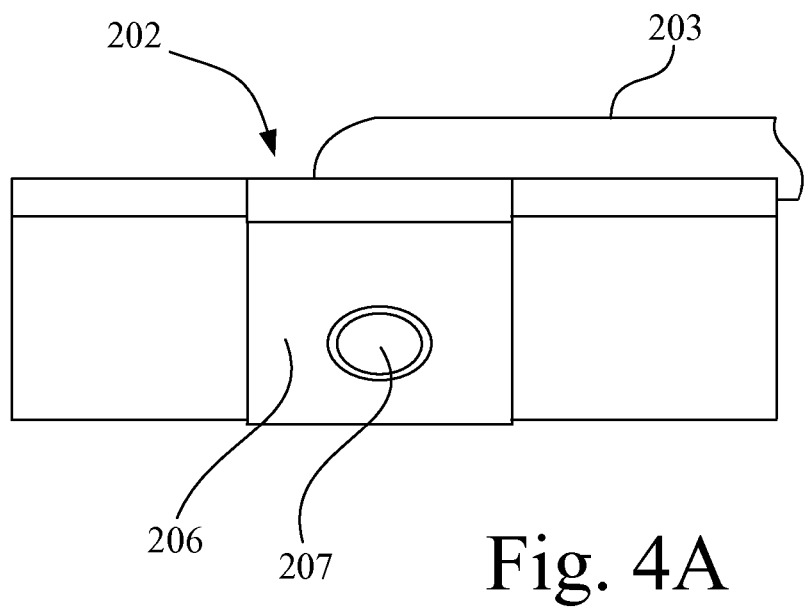
FIG. 4A is a perspective view of a vacuum seal element of the vacuum path of the driver assembly of FIG. 3.

First vacuum path 20 of driver assembly 12 is permanently associated with vacuum source 18. First vacuum path 20, also sometimes referred to as a non-disposable vacuum path, has a proximal end 201 and a distal end 202, and includes, for example, conduits 203, a first one-way valve 204, and a particulate filter 205. Proximal end 201 is fixedly coupled to vacuum source 18 in fluid communication therewith, e.g., is fixedly connected to vacuum source port 181 of vacuum source 18. Referring also to FIG. 4A, distal end 202 includes a first vacuum seal element 206. In the present embodiment, first vacuum seal element 206 is a planar abutment surface that surrounds a first passageway 207 of first vacuum path 20.

First one-way valve 204 is configured and arranged to permit a negative pressure fluid flow toward vacuum source 18 and to prevent a positive pressure fluid flow away from vacuum source 18 toward the distal end 202 of first vacuum path 20. The first one-way valve 204 may be, for example, a check-valve, such as a ball valve or reed valve, that opens with a fluid flow toward vacuum source 18, and closes in the case of a reverse (positive) flow away from vacuum source 18.

In the present embodiment, particulate filter 205 is located between vacuum source 18 and distal end 202 of first vacuum path 20. Particulate filter 205 may be, for example, a mesh screen formed from metal or plastic. However, it is contemplated that particulate filter 205 may be located in fluid management system 16 between vacuum source 18 and a vacuum receiving component of biopsy probe assembly 14.

The vacuum monitoring mechanism 30 is coupled to vacuum source 18 to shut off vacuum source 18 when a sensed vacuum level has fallen below a threshold level. Vacuum monitoring mechanism 30 may include, for example, a vacuum monitor and control program executing on controller 26, and a pressure sensor 301 coupled to controller 26, and in fluid communication with first vacuum path 20 for detecting a pressure in first vacuum path 20. If, for example, the vacuum flow level in first vacuum path 20 falls below a predetermined level, indicating a restriction in fluid management system 16, controller 26 may respond by shutting off vacuum source 18, e.g., turning off electric motor 183. Alternatively, controller 26 may monitor the current supplied to electric motor 183, and if the current exceeds a predetermined amount, indicating a restriction in fluid management system 16, controller 26 may respond by shutting off vacuum source 18, e.g., turning off electric motor 183.

The disposable biopsy probe assembly 14 is configured for releasable attachment to driver assembly 12. As used herein, the term "releasable attachment" means a configuration that facilitates an intended temporary connection followed by selective detachment involving a manipulation of disposable biopsy probe assembly 14 relative to driver assembly 12, without the need for tools.

The disposable biopsy probe assembly 14 includes a frame 141 to which a transmission device 42, a biopsy probe 44, and the second vacuum path 22 are mounted. Biopsy probe 44 is drivably coupled to transmission device 42, and transmission device 42 is drivably coupled to electromechanical power source 28 of driver assembly 12.

In the embodiment shown, transmission device 42 includes a first driven unit 421 and a second driven unit 422 that are drivably engaged with various components of biopsy probe 44. Also, first driven unit 421 is drivably engaged with first drive 361 of electrical drive assembly 36 of driver assembly 12. Second driven unit 422 is drivably engaged with second drive 362 of electrical drive assembly 36 of driver assembly 12.

In the embodiment shown (see, e.g., FIGS. 1-3), biopsy probe 44 includes a sample basket 441 and a cutter cannula 442. Sample basket 441 has a sharpened tip 443 to aid in puncturing tissue and has a sample notch 444 in the form of a recessed region for receiving a biopsy tissue sample. Sample basket 441 and a cutter cannula 442 are configured to be individually movable along a longitudinal axis 445.

In operation, cutter cannula 442 is linearly driven by first driven unit 421 to traverse over sample notch 444 of sample basket 441 along longitudinal axis 445. For example, first driven unit 421 may be in the form of a linear slide that is drivably engaged with first drive 361 of driver assembly 12, which in turn drives cutter cannula 442 along longitudinal axis 445 in a first direction 46, i.e., toward a proximal end of driver assembly 12, to expose sample notch 444 of sample basket 441, and drives cutter cannula 442 in a second direction 48 opposite to first direction 46 to sever tissue prolapsed into sample notch 444. Also, first driven unit 421 and second driven unit 422 may be configured to operate in unison to advance both sample basket 441 and cutter cannula 442 in unison along an longitudinal axis 445 in a piercing shot operation to aid in inserting biopsy probe 44 into fibrous tissue.

The second driven unit 422 may include a flexible toothed rack 50 and a gear train 52. Flexible toothed rack 50 is connected to sample basket 441, and gear train 52 is engaged with the teeth of flexible toothed rack 50. In operation, second drive 362 transfers rotary motion to gear train 52, and in turn gear train 52 engages flexible toothed rack 50 to move sample basket 441 linearly to transport the tissue captured in sample notch 444 out of the body of the patient. Flexible toothed rack 50 is received in a coiling unit 54 when retracting, thereby enabling substantial reduction in the overall device length of biopsy apparatus 10 as compared to a rigid capture system. Each harvested tissue sample is transported out of the body of the patient and is collected by tissue sample retrieval mechanism 56, which scoops the tissue sample out of sample notch 444.

In the present embodiment, coiling unit 54 and tissue sample retrieval mechanism 56 are as an integral unit with housing 57 that is common to coiling unit 54 and tissue sample retrieval mechanism 56. Housing 57 is attached to frame 141. Tissue sample retrieval mechanism 56 will be described in greater detail later. As shown, for example, in FIGS. 2, 5A and 6-8, housing 57 has a distinct shape S1 as a combination of curved and flat surfaces with an overall height H1, length L1, and width W1 dimensions which in combination define a unique profile of housing 57.

In the present embodiment, the second vacuum path 22, also sometimes referred to as a disposable vacuum path 22, has a first end 221 and a second end 222, and includes for example, conduits 223, a second one-way valve 224, and a fluid management tank 225. The first end 221 is configured for removable attachment to the distal end 202 of the first vacuum path 20 of driver assembly 12. The second end 222 is coupled in fluid communication with sample basket 441, and more particularly, is coupled in fluid communication with sample notch 444 of sample basket 441.

Figure 4B:
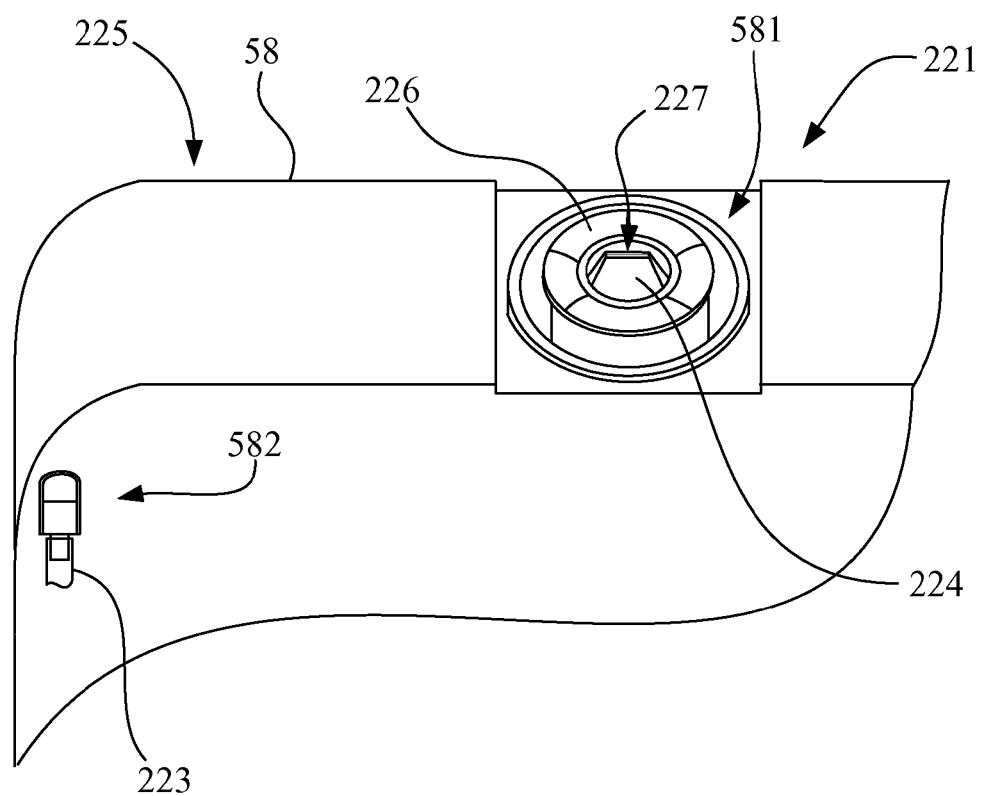
FIG. 4B is a perspective view of a vacuum seal element of the vacuum path of the disposable biopsy probe of FIG. 3.

Referring also to FIG. 4B, the first end 221 of the disposable vacuum path 22 includes a second vacuum seal element 226. The first vacuum seal element 206 of the driver assembly 12 contacts the second vacuum seal element 226 of the disposable biopsy probe assembly 14 in sealing engagement when the disposable biopsy probe assembly 14 is attached to driver assembly 12. The second vacuum seal element 226 is a compliant, e.g., rubber, annular member that surrounds a second passageway 227 of the second vacuum path 22.

The second one-way valve 224 configured and arranged to permit the negative pressure fluid flow from sample basket 441 toward the first end 221 of the second vacuum path 22, and to redundantly (in conjunction with first one-way valve 204 of driver assembly 12) prevent any positive pressure fluid flow in a direction from the first end 221 of the second vacuum path 22 toward sample basket 441. In other words, the second one-way valve 224 provides a redundant second level of protection in preventing any positive pressure from reaching sample notch 444 of sample basket 441. In the present embodiment, the second one-way valve 224 may be, for example, a duckbill valve, e.g., a reed-type valve, that opens with a fluid flow out the bill portion of the duckbill valve, and closes with a reverse flow. As shown, the second one-way valve 224 may be positioned within the second vacuum seal element 226 at first end 221 of second vacuum path 22.

Figure 5A:
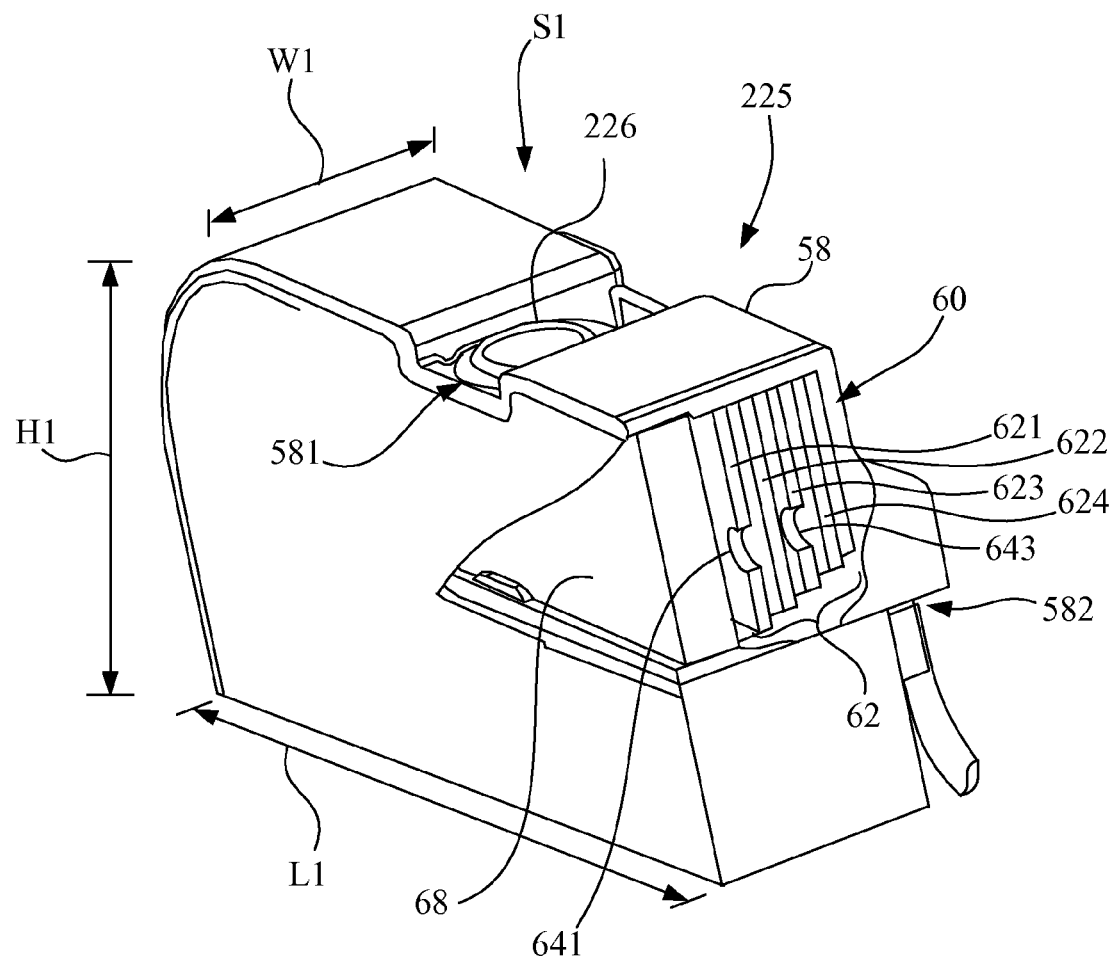
FIG. 5A is a perspective view of the fluid management tank of the disposable biopsy probe shown in FIGS. 2 and 3, with a portion broken away to expose a filter arrangement.

Referring also to FIG. 5A, fluid management tank 225 is fluidically interposed in the second vacuum path 22 between the first end 221 and the second end 222. Fluid management tank 225 includes a body 58 and a filter arrangement 60 contained within body 58 configured to prevent a flow of residual biopsy biological material, e.g., blood and particulate matter, from sample notch 444 of sample basket 441 to vacuum source 18 of driver assembly 12.

Body 58 of fluid management tank 225 has a first port 581 and a second port 582, with the second vacuum path 22 continuing between the first port 581 and the second port 582. The second port 582 of fluid management tank 225 is coupled to sample basket 441. Each of the second one-way valve 224 and the second vacuum seal element 226 of the second vacuum path 22 is coupled to the first port 581 of fluid management tank 225, and in the present embodiment, is mounted to an external surface of body 58 of fluid management tank 225.

Figure 5B:
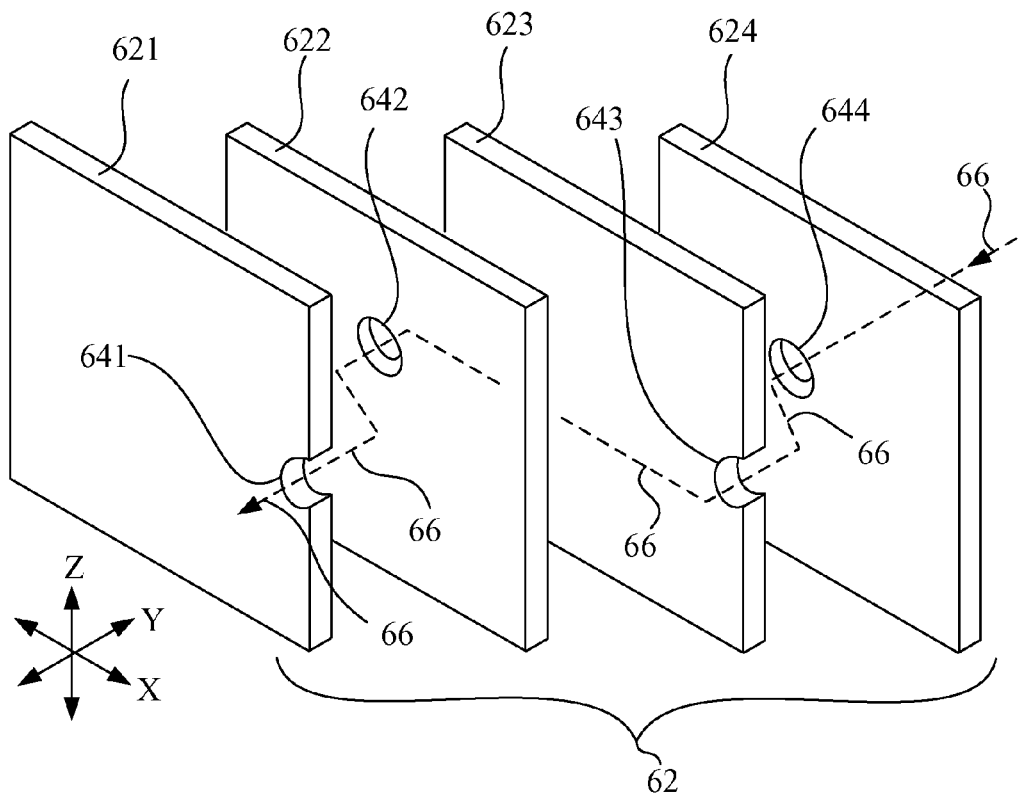
FIG. 5B is an exploded view of a plurality of fluid absorption layers of the filter arrangement of FIG. 5A.

As illustrated in FIGS. 5A and 5B, filter arrangement 60 includes a plurality of fluid absorption layers 62, individually identified as layers 621, 622, 623 and 624, arranged side by side, with each fluid absorption layer 621, 622, 623 and 624 being spaced apart from an adjacent fluid absorption layer e.g., 621 to 622, 622 to 623, 623, to 624. Each fluid absorption layer 621, 622, 623 and 624 has a respective through opening 641, 642, 643, 644, wherein adjacent through openings of through openings 641, 642, 643, 644 of the plurality of fluid absorption layers 62 are offset one to the next, e.g., in at least one of an X, Y, and Z direction, to form a tortuous open fluid passageway 66 through the plurality of fluid absorption layers 62. Each fluid absorption layer 621, 622, 623 and 624 may be, for example, a blotting paper.

Figure 5C:
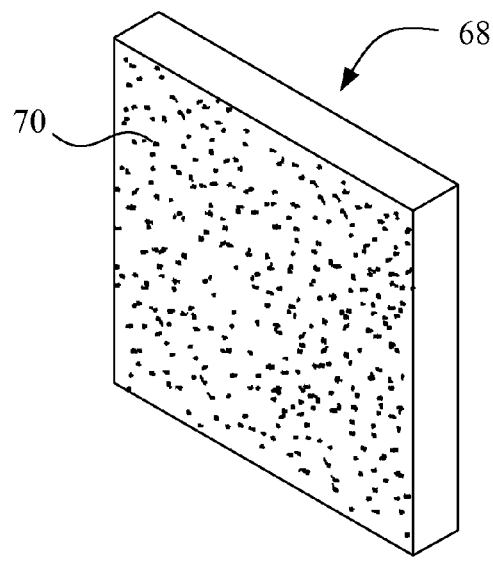
FIG. 5C is a perspective view of a porous filter element of the filter arrangement of FIG. 5A.

As illustrated in FIGS. 5A and 5C, filter arrangement 60 may further include a porous filter element 68 arranged to be fluidically in series with the plurality of fluid absorption layers 62 along the second vacuum path 22 that defines second passageway 227. The porous filter element 68 exhibits increased restriction to fluid flow as an increased number of pores 70 in the porous filter element 68 become clogged by residual biopsy biological material, such as blood and tissue particles. When a volume of the fluid flow through fluid management tank 225 has been reduced to a predetermined level, vacuum monitoring mechanism 30 senses the vacuum restriction, and controller 26 responds to shut off vacuum source 18.

Referring to FIGS. 6-13, each harvested tissue sample is transported out of the body of the patient and is collected by tissue sample retrieval mechanism 56. In general, tissue sample retrieval mechanism 56 collects tissue samples that have been harvested by scooping the tissue sample out of sample notch 444 of sample basket 441 of biopsy probe 44.

Figure 6:
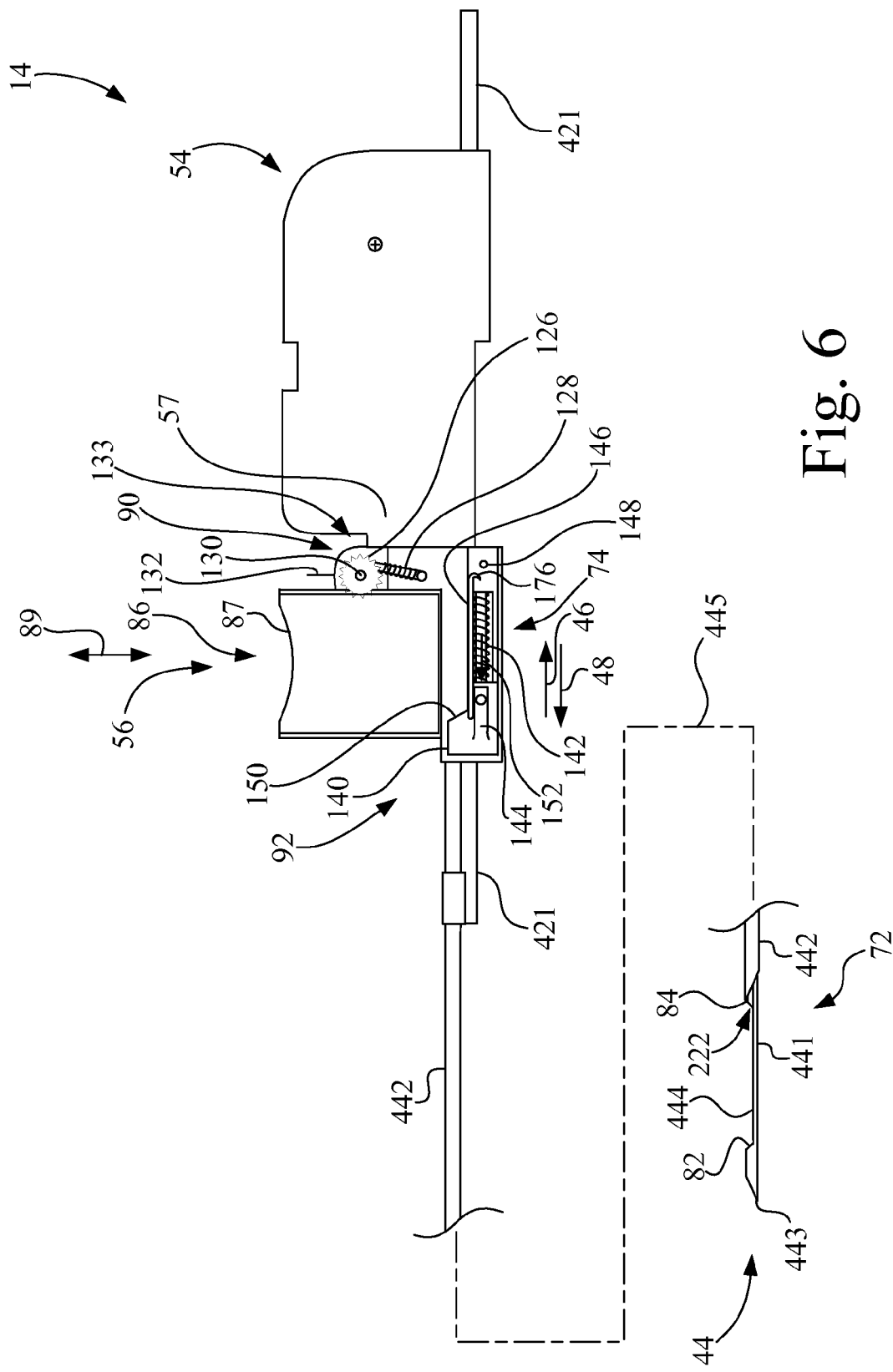
FIG. 6 is a side view of the disposable biopsy probe of FIG. 2 showing in further detail a tissue sample retrieval mechanism with the sample collection tank removed.
Figure 7:
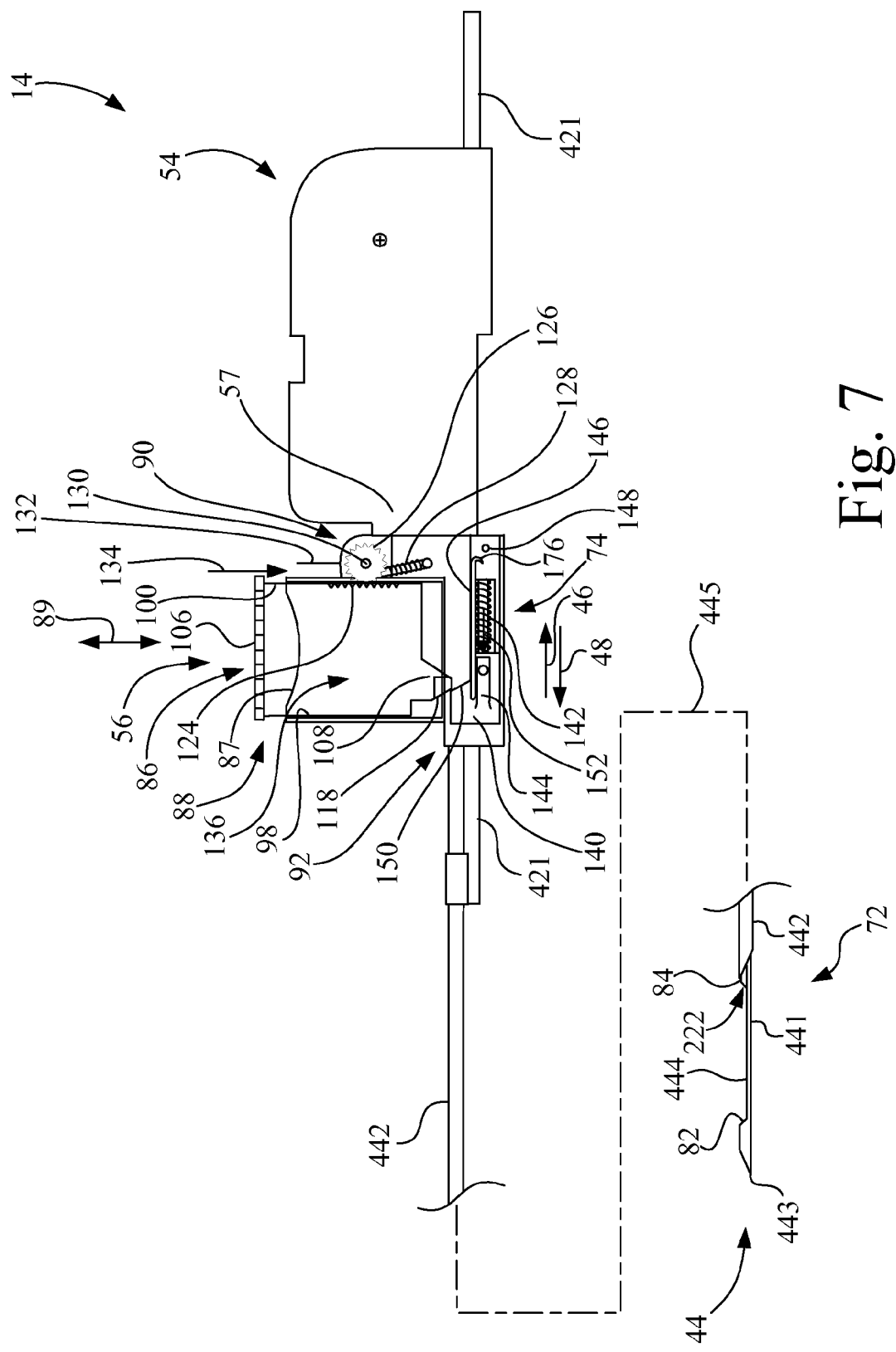
FIG. 7 is a side view of the disposable biopsy probe of FIG. 6 showing the tissue sample retrieval mechanism with the sample collection tank installed, and with the sample collection tank in the raised position.
Figure 8:
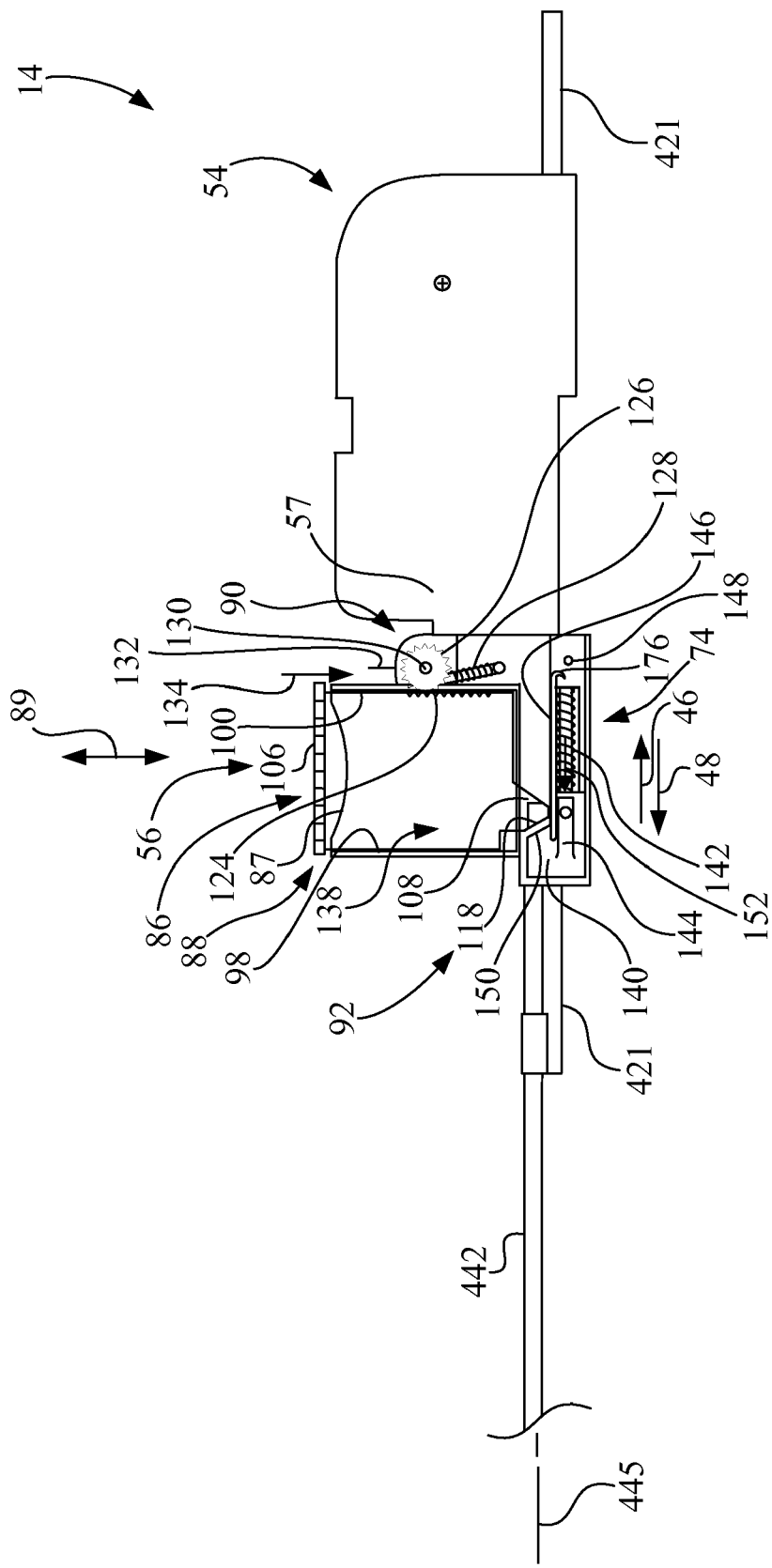
FIG. 8 is a side view of the disposable biopsy probe of FIG. 6 showing the tissue sample retrieval mechanism with the sample collection tank installed, and with the sample collection tank in the lowered collection position.
Figure 12:
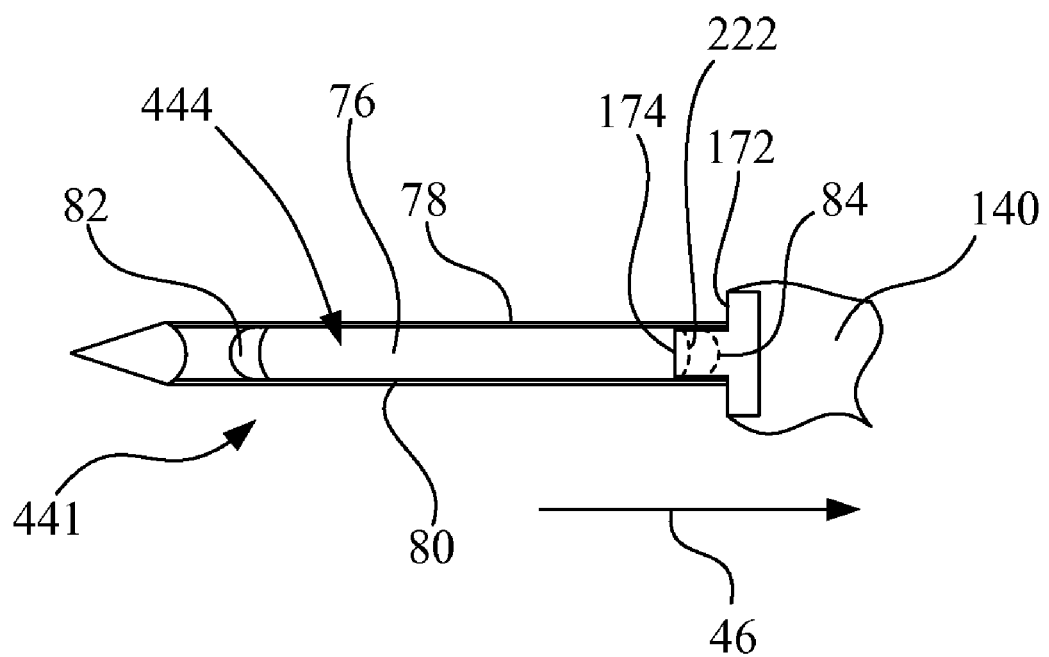
FIG. 12 is a top view of the sample basket and the lift member of the disposable biopsy probe of FIG. 7, with a portion of lift member broken away to expose a T-shaped stop, and a leaf spring tongue forming a portion of the T-shaped stop for removing residual tissue material and debris from a vacuum path at the sample notch of the sample basket.

Referring to FIGS. 6-9, biopsy probe 44 of probe assembly 14 includes a biopsy cannula, e.g., cutter cannula 442, and sample basket 441 arranged coaxially about longitudinal axis 445. Sample basket 441 having sample notch 444 is movably disposed relative to biopsy cannula 442 along longitudinal axis 445 from a tissue harvesting position 72, as shown in FIGS. 6 and 7, to a tissue sample retrieval region 74, as illustrated in FIGS. 6-8 by electromechanical power source 28 and second drive 362, as more fully described above with respect to FIG. 3. Referring also to FIGS. 10 and 12, sample notch 444 is an elongate recessed region of sample basket 441 having a generally semicircular cross-section, and has a recessed floor 76, a pair of spaced elongate edges 78, 80 on opposite sides of recessed floor 76, a leading transition bevel 82, and a trailing transition bevel 84. Leading transition bevel 82 and trailing transition bevel 84 are located at opposite ends of the elongate recessed region, i.e., sample notch, 444.

In the present embodiment, tissue sample retrieval mechanism 56 includes a sample tank receptacle 86, a sample collection tank 88, a toggle mechanism 90, and a tank positioning mechanism 92. Sample collection tank 88 is configured for removable insertion into sample tank receptacle 86.

Sample tank receptacle 86, which may be formed integral with housing 57, includes a hollow guide 87 size to slidably receive sample collection tank 88. Thus, the configuration of sample tank receptacle 86 is such that sample tank receptacle 86 permits bi-directional movement of sample collection tank 88 in directions 89 (signified by double headed arrow) that are substantially perpendicular to longitudinal axis 445. Also, the configuration of sample tank receptacle 86 is such that sample tank receptacle 86 prohibits movement of sample collection tank 88 in a direction 46 or 48 along longitudinal axis 445.

Sample collection tank 88 defines a single collection cavity 94 (see FIG. 9) configured for receiving multiple tissue samples, such as tissue sample TS. Sample collection tank 88 has, in forming collection cavity 94, a base 96, a front wall 98, a rear wall 100, a pair of side walls 102, 104, and a removable cap 106. Sample collection tank 88 further includes a tissue sample scoop 108. Sample collection tank 88 is configured to collect a tissue sample directly from sample notch 444 as sample basket 441 moves along longitudinal axis 445 at tissue sample retrieval region 74. In this regard, tissue sample scoop 108 of sample collection tank 88 is configured to engage sample notch 444 of sample basket 441.

Tissue sample scoop 108 is fixed to and projects downwardly from base 96. Tissue sample scoop 108 extends forward toward a front portion 110 of sample collection tank 88 to terminate at a rim 112. Tissue sample scoop 108 has a tissue collection lumen 114 through which each tissue sample TS harvested by biopsy probe assembly 14 will pass. Tissue collection lumen 114 begins at an opening 116 located near rim 112 and extends to collection cavity 94. Tissue sample scoop 108 has a ramped face 118 located adjacent rim 112. Also, tissue sample scoop 108 has a first shoulder 120 and a second shoulder 122 that are positioned on opposite sides of opening 116.

A rack gear 124 is longitudinally (e.g., vertically) positioned on rear wall 100 of sample collection tank 88 to engage toggle mechanism 90.

Referring to FIGS. 6-9, toggle mechanism 90 is configured to aid in the mounting of sample collection tank 88 in sample tank receptacle 86, and to aid in the removal of sample collection tank 88 from sample tank receptacle 86. Toggle mechanism 90 is mounted to housing 57 and includes a rotary gear 126 and a spring 128. Rotary gear 126 has a rotational axis 130, e.g., an axle, which is attached to, or formed integral with, housing 57. Spring 128 is coupled between rotary gear 126 and housing 57, and is eccentrically mounted to rotary gear 126, i.e., at a location offset from rotational axis 130. Rotary gear 126 is located for driving engagement with rack gear 124 of sample collection tank 88, as sample collection tank 88 is slidably received by sample tank receptacle 86.

Referring to FIGS. 6-8, toggle mechanism 90 is configured to define a break-over point 132, e.g., at the 12:00 o'clock position in the orientation as shown. FIG. 6 shows an orientation of toggle mechanism 90 when sample collection tank 88 is not installed in hollow guide 87 of sample tank receptacle 86, where spring 128 is positioned beyond the 12 o'clock position in a clockwise direction in the orientation as shown, thus defining a home position 133 for toggle mechanism 90.

FIG. 7 shows an orientation of toggle mechanism 90 when sample collection tank 88 is installed (inserted) in hollow guide 87 of sample tank receptacle 86. As sample collection tank 88 is inserted in hollow guide 87 of sample tank receptacle 86, rack gear 124 of sample collection tank 88 engages rotary gear 126 and rotates rotary gear 126 about rotational axis 130 in the counterclockwise direction in the orientation as shown. When spring 128 is moved beyond break-over point 132, e.g., the 12 o'clock position, in the counterclockwise direction as sample collection tank 88 is slidably received by sample tank receptacle 86, spring 128 provides a biasing force 134, e.g., a downward pressure, via rotary gear 126 to bias sample collection tank 88 downwardly toward longitudinal axis 445. Thus, biasing force 134 exerts downward pressure on sample collection tank 88 when spring 128 is moved beyond the 12 o'clock position in the counterclockwise direction, in the orientation as shown in FIG. 7, and biasing force 134 is maintained when sample collection tank 88 is installed in sample tank receptacle 86.

Figure 9:
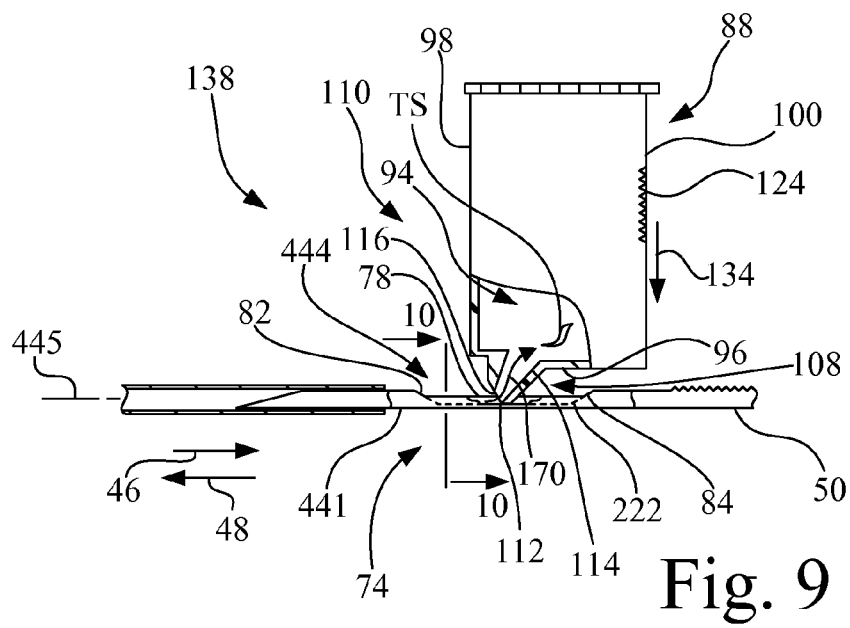
FIG. 9 is a side view of a portion of the tissue sample retrieval mechanism of FIG. 8 with a portion of the cutter cannula sectioned away to expose the retracting sample basket, and with a portion of the sample basket broken way to show the interaction of the tissue sample scoop of the sample collection tank with the sample notch.
Figure 11:
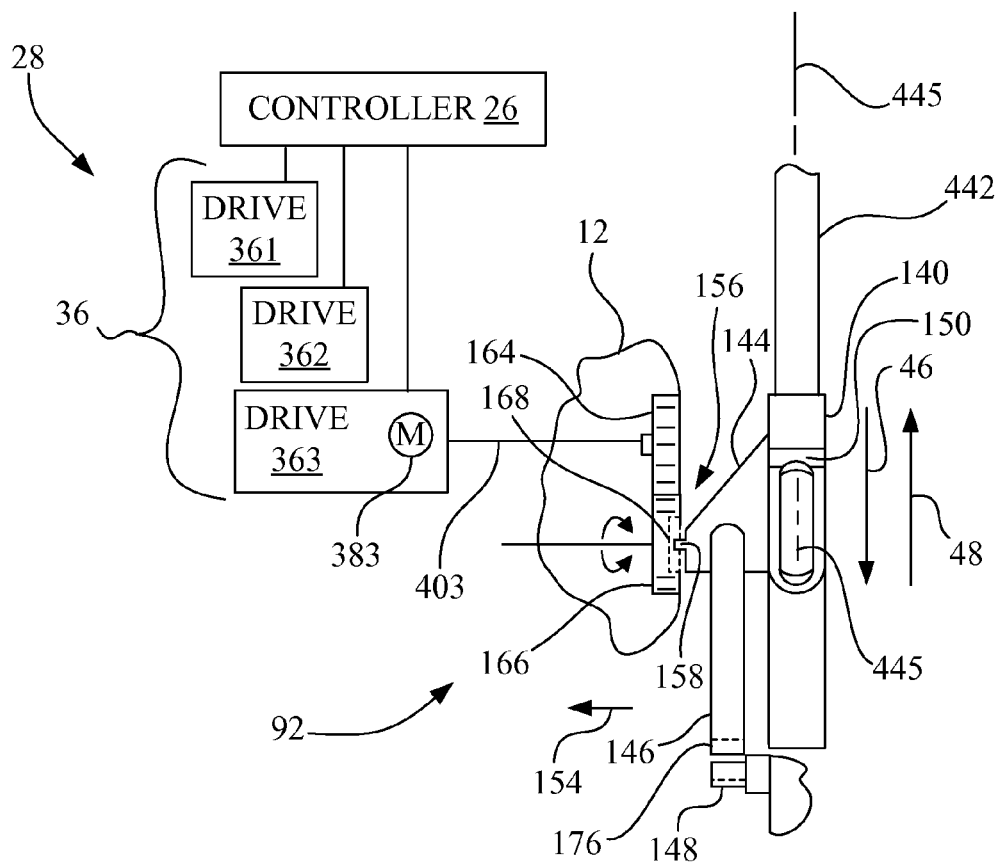
FIG. 11 is a top view of tank positioning mechanism of FIG. 8.
Figure 10:
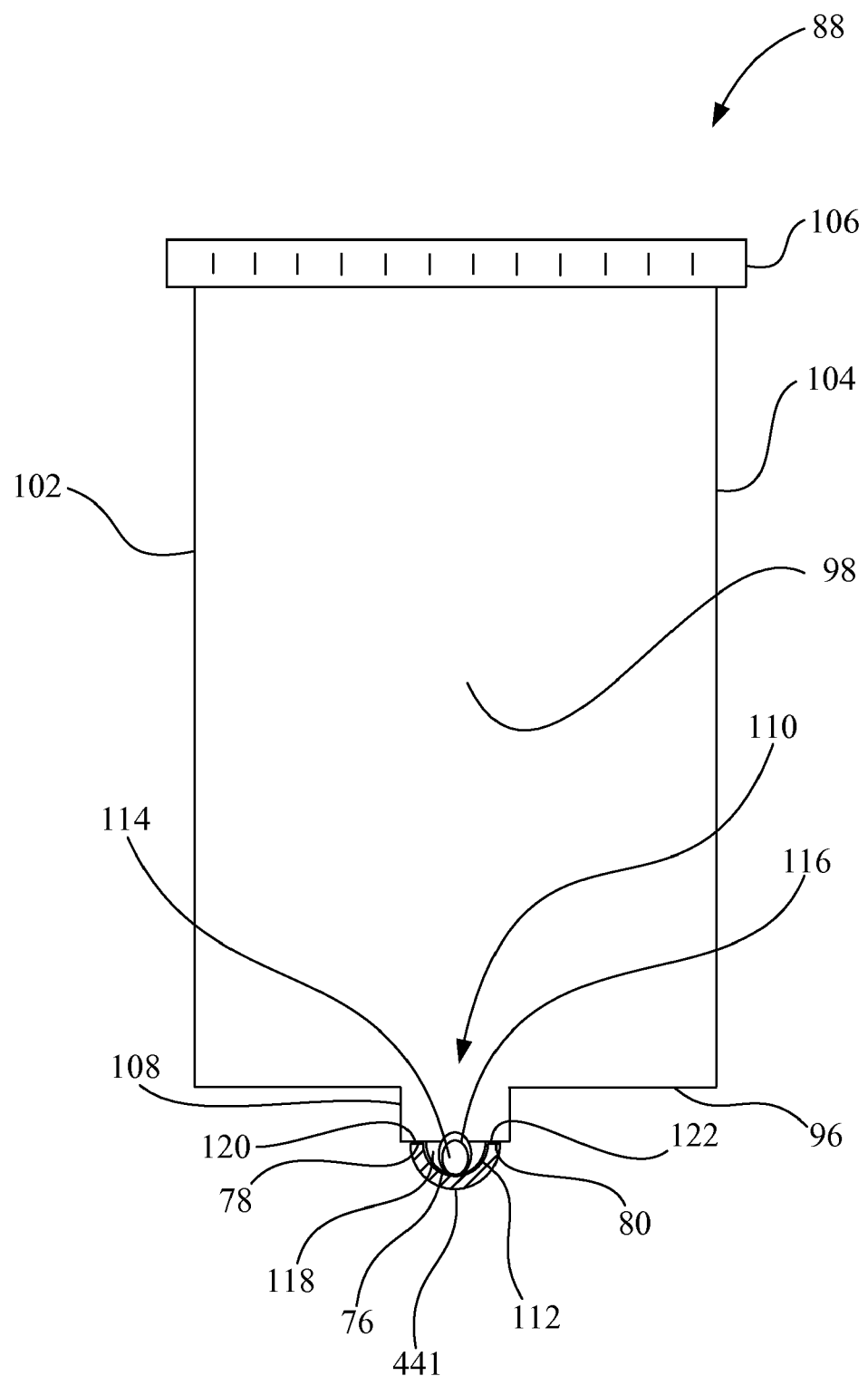
FIG. 10 is an enlarged front view of the sample collection tank of FIG. 9 showing the interaction of the rim of the sample collection tank with the sample basket shown in section along line 10-10 of FIG. 9.

Referring to FIG. 11 in conjunction with FIGS. 7-9, tank positioning mechanism 92 is configured to selectively move sample collection tank 88 between a raised position 136 illustrated in FIG. 7 and a lowered position 138 illustrated in FIGS. 8 and 9.

Tank positioning mechanism 92 is drivably engaged with electromechanical power source 28 to selectively lower, in conjunction with toggle mechanism 90, sample collection tank 88 from raised position 136 to lowered position 138 to position a portion, i.e., tissue sample scoop 108, of sample collection tank 88 in sliding engagement with sample notch 444 to facilitate collection of a tissue sample, e.g., tissue sample TS, from sample basket 441 as sample basket 441 is moved in tissue sample retrieval region 74. Also, electromechanical power source 28 is drivably engaged with tank positioning mechanism 92 and/or flexible toothed rack 50 to selectively raise sample collection tank 88, against the biasing force 134 exerted by toggle mechanism 90 and the biasing force 152 exerted by tank positioning mechanism 92, from lowered position 138 to raised position 136 to disengage sample collection tank 88 from sample notch 444 of sample basket 441 prior to, and following, tissue collection from sample basket 441.

More particularly, referring to FIGS. 6-8 and 11, tank positioning mechanism 92 includes a lift member 140, a spring 142, a lever 144, a latch member 146 and a latch catch 148.

Referring to FIGS. 7 and 8, lift member 140 is positioned along longitudinal axis 445. Lift member 140 has a ramp surface 150 positioned to engage ramped face 118 of sample collection tank 88. Spring 142 is positioned between lift member 140 and housing 57 to exert biasing force 152 on lift member 140 to bias ramp surface 150 in a direction away from ramped face 118 of sample collection tank 88.

As shown in FIG. 11, lever 144 extends from lift member 140 in a direction 154 perpendicular to longitudinal axis 445. Lever 144 has a distal end 156 configured to engage electromechanical power source 28, which may be in the form of a pin 158.

Electromechanical power source 28 is operable to move lift member 140 along longitudinal axis 445 in direction 46 to lift sample collection tank 88 away from longitudinal axis 445 as ramp surface 150 of lift member 140 slides along ramped face 118 of sample collection tank 88. Likewise, electromechanical power source 28 is operable to move lift member 140 along longitudinal axis 445 in direction 48 opposite first direction 46 to lower sample collection tank 88 toward longitudinal axis 445 as ramp surface 150 of lift member 140 slides along ramped face 118 of sample collection tank 88.

As shown in FIG. 11, electromechanical power source 28 includes a lift drive 363 having an electrical motor 383 coupled to a motion transfer unit 403 (shown schematically in part by a line) that generally terminates at gears 164 and 166. Gear 166 includes a slot 168 for engaging pin 158 of lever 144. Motion transfer unit 403 provides rotary motion to gear 164, which in turn imparts rotary motion to gear 166. Motion transfer unit 403 may include one or more of a gear, gear train, belt/pulley arrangement, etc., for effecting at least a partial rotation of gear 164. Gear 166, however, is only rotated at a partial revolution, so as to effect a linear translation of pin 158 of lever 144, and in turn a linear translation of lift member 140.

The lowering of sample collection tank 88 for tissue sample collection (retrieval) is initiated by electromechanical power source 28 wherein gear 166 of lift drive 363 of electromechanical power source 28 is rotated in a direction to translate the lever 144, and in turn lift member 140, in direction 48 to lower sample collection tank 88. Biasing force 152 exerted on lift member 140 aids in moving ramp surface 150 in direction 48 away from ramped face 118 of sample collection tank 88. At this time, first shoulder 120 and second shoulder 122 of tissue sample scoop 108 are positioned for respective sliding engagement with the pair of spaced elongate edges 78, 80 of the elongate recessed region of sample notch 444 of sample basket 441 along longitudinal axis 445.

More particularly, with reference to FIGS. 8 and 11, the translation of the lever 144 and in turn lift member 140 in direction 48 causes the oblique face ramped face 118 of sample collection tank 88 to slide down the oblique ramp surface 150 of lift member 140, and tissue sample scoop 108 with rim 112 are moved into the elongate recessed region of sample notch 444 of sample basket 441 toward recessed floor 76. Referring also to FIGS. 9 and 10, continued transport of the sample notch 444 in direction 46 by electromechanical power source 28 will cause rim 112 of tissue sample scoop 108 to slide along recessed floor 76 and along the sides between elongate edges 78, 80 of sample notch 444, scooping up the tissue sample TS and transporting the tissue sample TS through tissue collection lumen 114 into collection cavity 94 of sample collection tank 88 along path 170. The shoulders 120, 122 of sample collection tank 88 are configured to slide along the upper spaced elongate edges 78, 80 of sample basket 441, ensuring that no tissue sample material is pushed out of sample notch 444.

The raising of sample collection tank 88 occurs near the conclusion of the tissue collection sequence. Near the conclusion of the tissue collection sequence, the further movement of sample notch 444 of sample basket 441 in direction 46 by operation of electromechanical power source 28 and second drive 362 is transferred to lift member 140 by a driving engagement of sample basket 441 in direction 46 with a T-shaped stop 172 (see FIG. 12) attached to lift member 140, causing lift member 140 to move in direction 46. The scoop rim 112 of sample collection tank 88 reaches the sloping leading transition bevel 82 of sample notch 444 and is pushed upwards by the interplay between ramped face 118 of sample collection tank 88 and leading transition bevel 82 of sample notch 444, thus beginning to raise sample collection tank 88. As lift member 140 is further moved in direction 46 by movement of sample notch 444, the scoop rim 112 leaves sample notch 444 and ramped face 118 of sample collection tank 88 and comes to rest against ramp surface 150 of lift member 140, which closes off tissue collection lumen 114 of sample collection tank 88 and prevents the tissue sample TS from falling out of tissue collection lumen 114.

In addition, lift drive 363 is rotated to ensure that lift member 140 is translated fully in direction 46 in the event that the force exerted by sample notch 444 is insufficient to accomplish the translation. More particularly, electromechanical power source 28 rotates gear 166 of lift drive 363 in a direction to translate the lever 144 in direction 46. Thus, electromechanical power source 28 facilitates movement of lift member 140 along longitudinal axis 445 in first direction 46 against the biasing force 152 exerted by spring 142 to lift sample collection tank 88 as ramp surface 150 of lift member 140 slides along ramped face 118 of sample collection tank 88.

At the conclusion of the transport of sample notch 444 in direction 46 towards the proximal end of driver assembly 12, a leaf spring tongue 174 of T-shaped stop 172 (see FIG. 12) removes residual tissue material and debris from the second end 222 of vacuum path 22 at trailing transition bevel 84 of sample notch 444 to ensure that a sufficient vacuum may be drawn into sample notch 444.

Referring again to FIGS. 6-8, 11 and 13, latch member 146 is attached to, or formed integral with, lift member 140. Latch member 146 extends from lever 144 in direction 46, and has a distal hook 176. Latch member 146 is located for engagement with latch catch 148 to latch lift member 140 in a transport latched position, shown in FIG. 13, corresponding to raised position 136 of sample collection tank 88. Latch catch 148 may be attached to, or formed integral with, housing 57.

Figure 13:
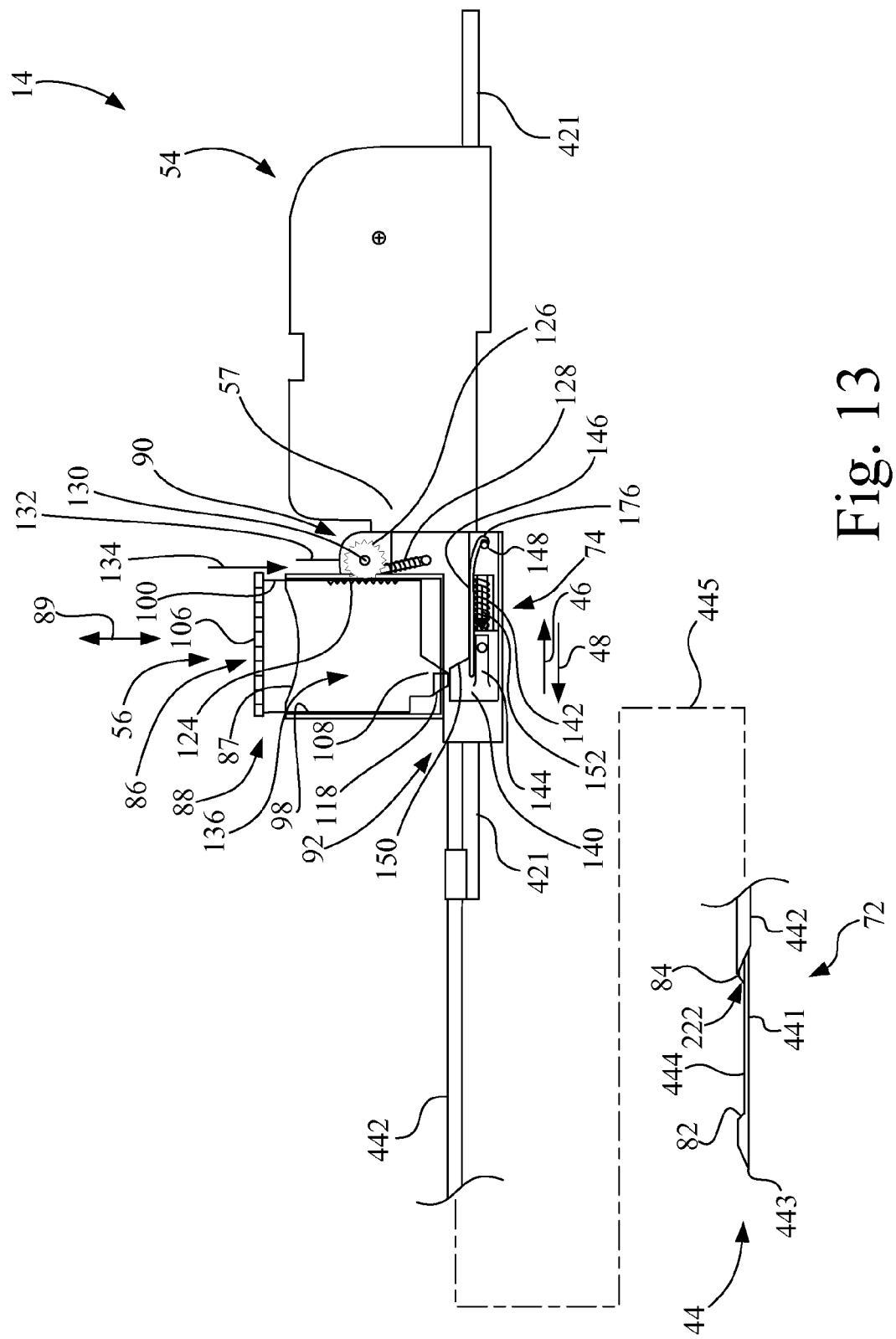
FIG. 13 is a side view of the disposable biopsy probe of FIG. 7 showing the latch member of the tank positioning mechanism in the latched transport position.

One purpose of latch member 146 is to maintain the proper insertion position of lever 144 during transport of biopsy probe assembly 14 to ensure proper insertion of biopsy probe assembly 14 in driver assembly 12. Prior to insertion of biopsy probe assembly 14 in driver assembly 12, lever 144 is held in a latched transport position, which is the only position permitting pin 158 at distal end 156 of lever 144 to be inserted into slot 168 (e.g., a driver recess) of lift drive 363 (see FIG. 11). In the latched transport position, as illustrated in FIG. 13, the lever 144 is held in position by latch member 146 that is held in tension against latch catch 148 by pressure (biasing force 152) from spring 142. Thus, insertion of biopsy probe assembly 14 in driver assembly 12 in the latched transport position results in placement of pin 158 at distal end 156 of lever 144 in slot 168 (e.g., a driver recess) of lift drive 363.

A second purpose of the latch member 146 is to prevent accidental reuse of the disposable probe. As part of power up, the lift drive 363 engages pin 158 at distal end 156 of lever 144 and moves lever 144 in direction 46 to a fully retracted position, which in turn causes latch member 146 to move out of engagement with latch catch 148. The tension of the latch member 146 is released, causing latch member 146 to move out of the plane of latch catch 148 and preventing latch member 146 from reestablishing contact with latch catch 148. Since spring 142 will bias lift member 140 in direction 48, the latched transport position illustrated in FIG. 13 may not be reestablished once biopsy probe assembly 14 has been removed from driver assembly 12. Since the latched transport position is the only position permitting biopsy probe assembly 14 to be inserted in driver assembly 12, accidental reuse of biopsy probe assembly 14 is prevented.

Figure 14:
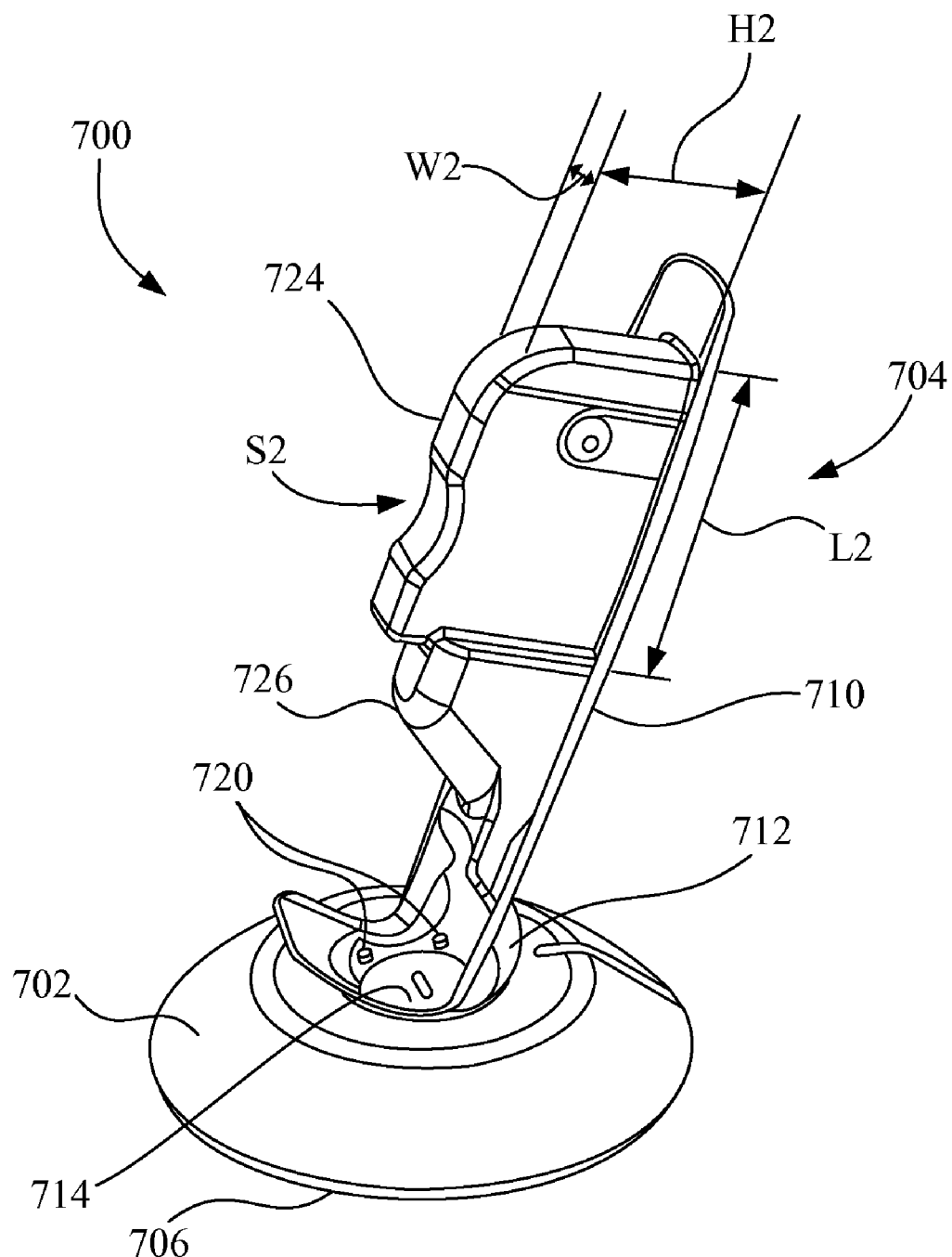
FIG. 14 is a perspective view of a charging station for use in charging the battery contained in the driver assembly of FIGS. 1 and 2.
Figure 15:
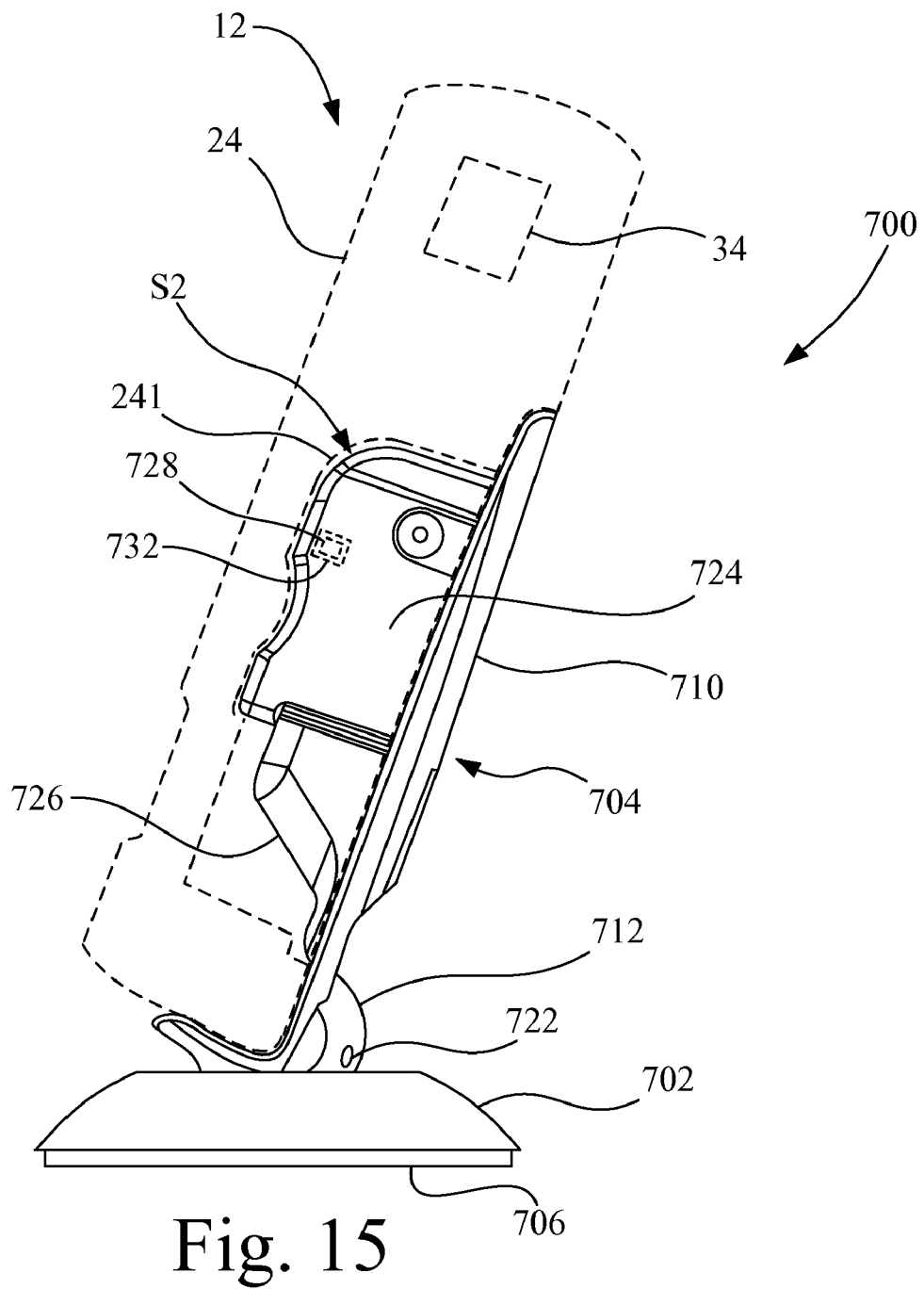
FIG. 15 is a side view of the charging station of FIG. 14 with the driver assembly shown in phantom lines in an installed position.
Figure 16:
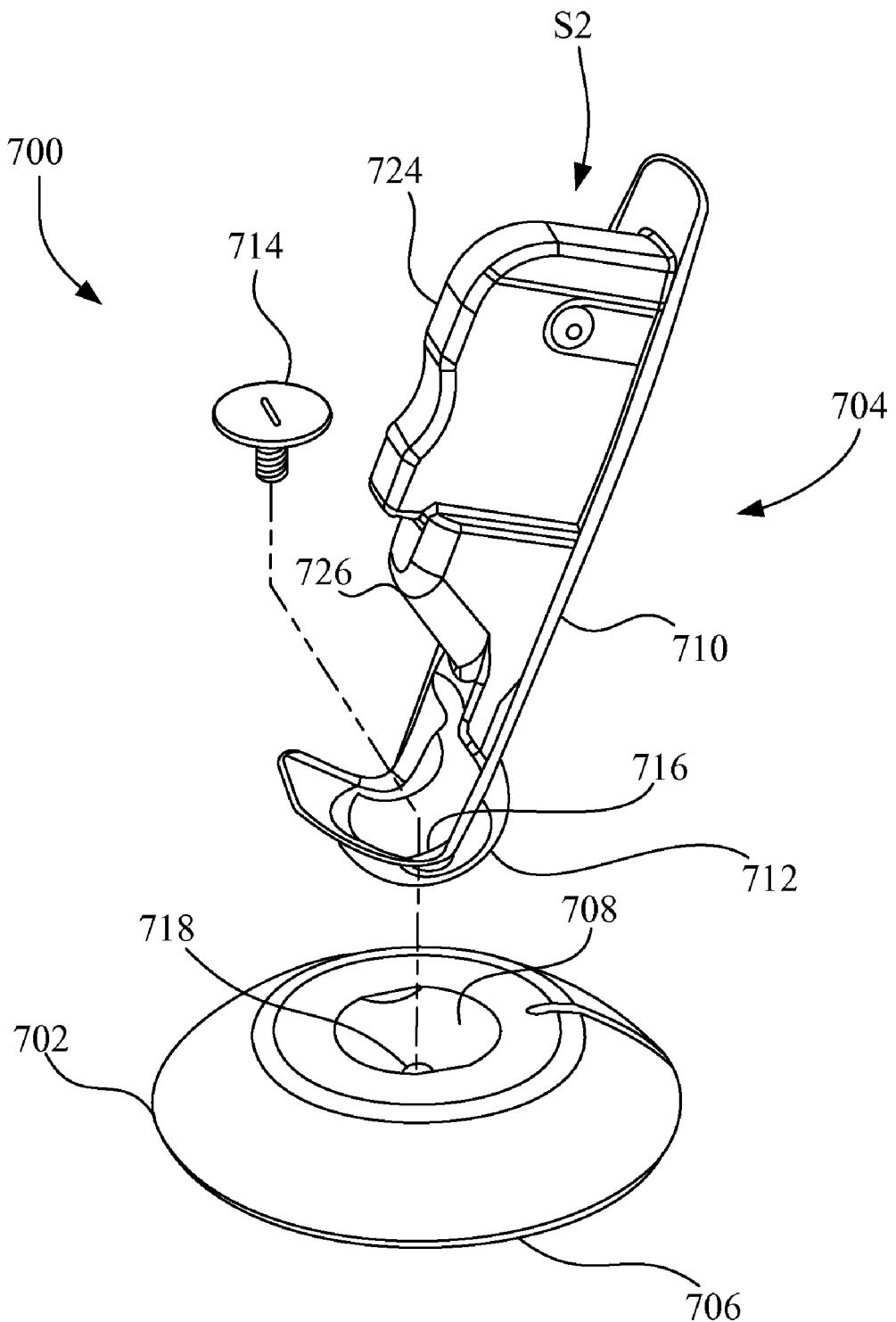
FIG. 16 is an exploded view of the charging station of FIG. 14.

FIGS. 14-23 relate to a charging station 700 used for automatically charging battery 34 of driver assembly 12. FIG. 14 illustrates charging station 700 in isolation, and FIG. 15 illustrates charging station 700 with driver assembly 12 removably mounted to charging station 700 for charging battery 34 of driver assembly 12. Referring also to FIG. 16, charging station 700 includes a base 702 and a charging dock 704.

Base 702 is of sufficient size and weight to ensure stability when charging station 700 is placed on a flat horizontal surface, such as a table top. Also, base 702 may include holes (not shown) to enable wall mounting of base 702 of charging station 700 in a vertical orientation. A protecting disc 706, which may be made of a rubber or rubber-like material, is mounted to base 702 to make charging station 700 slide-resistant when not permanently mounted to a mounting surface. Base 702 includes a concave receptacle 708 to facilitate a mounting of charging dock 704 in a pivoting relationship with respect to base 702.

Charging dock 704 includes a frame 710 which has a convex protrusion 712 configured for mating engagement with concave receptacle 708 of base 702. Charging dock 704 is guided relative to base 702 via a screw 714 that passes through a slotted opening 716 extending through convex protrusion 712, and with a threaded portion of screw 714 being received by corresponding threads of a threaded hole 718 located in concave receptacle 708 of base 702. At least one threaded knob 720 (two shown in FIG. 14) is threaded into corresponding holes 722 in convex protrusion 712, which when tightened engage concave receptacle 708 to maintain charging dock 704 in the chosen position relative to base 702. A loosing of knob 720 permits the pivoting of charging dock 704 to the desired angular position, e.g., 20 degrees as shown) relative to base 702.

A length and general shape of frame 710 corresponds to the length and general shape of frame 141 of biopsy probe assembly 14. Thus, frame 710 closes elongate cavity 241 in housing 24 of driver assembly 12 to protect the internal structure of driver assembly 12 when driver assembly 12 is placed on charging dock 704.

Charging dock 704 includes a housing 724 that is mounted to frame 710. Referring to FIG. 14, housing 724 has a distinct shape S2 as a combination of curved and flat surfaces, with an overall height H2, length L2, and width W2 dimensions, which in combination define a unique profile of housing 724. A nose portion 726 extends distally to housing 724, and generally corresponds to the location of sample tank receptacle 86 of biopsy probe assembly 14. Purposely, the shape S2 of housing 724 is substantially the same as the shape S1 of housing 57 of biopsy probe assembly 14 (see, e.g., FIG. 5A), making biopsy probe assembly 14 and charging dock 704 interchangeably insertable into cavity 241 of driver assembly 12 (e.g., compare FIGS. 2 and 15).

Figure 17:
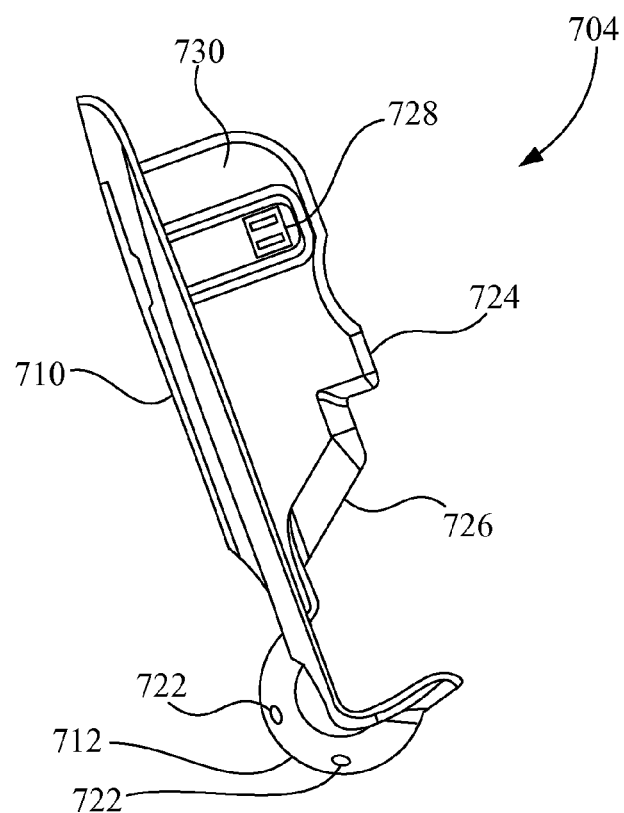
FIG. 17 is an opposite side view of the charging dock of the charging station of FIG. 14.
Figure 18:
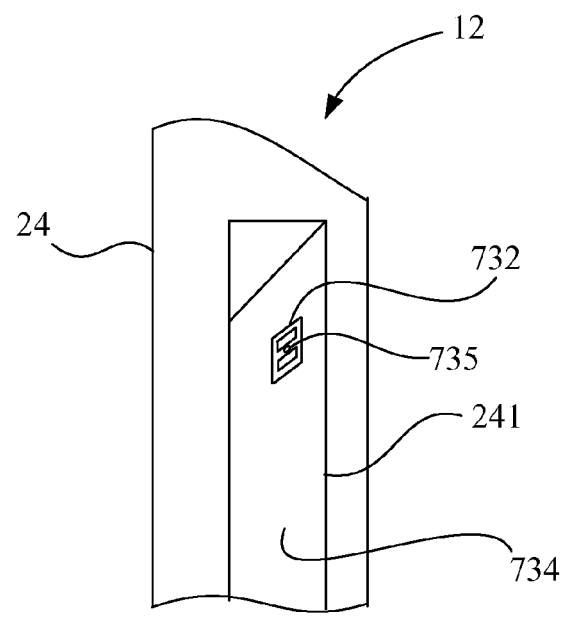
FIG. 18 is a bottom view of a portion of the housing of the driver assembly of FIG. 1.

Referring to FIGS. 15 and 17, a set of electrical contacts 728 is located to be accessible at a side wall 730 of housing 724 to facilitate electrical communication between charging station 700 and driver assembly 12 when driver assembly 12 is mounted on charging dock 704 for charging of battery 34. Correspondingly, as shown in FIG. 18, a corresponding set of electrical contacts 732 is positioned to be accessible through a side wall 734 of elongate cavity 241 of housing 24 of driver assembly 12 for engagement with the set of electrical contacts 728 of charging dock 704. Also, a manual software reset switch 735 may be positioned in the proximity of electrical contacts 732, or other location as desired, which may be manually actuated by a user using a small pointed object such as a straightened paper clip, to reset controller 26 to reboot the software executed by driver assembly 12.

Figure 19:
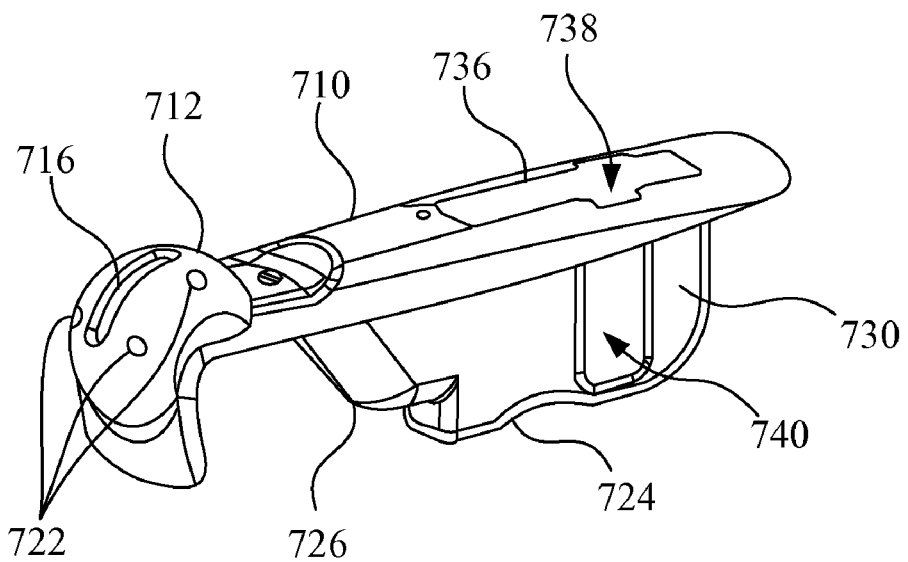
FIG. 19 is a bottom perspective view of the charging dock of FIG. 17 with a removable cover removed.
Figure 20:
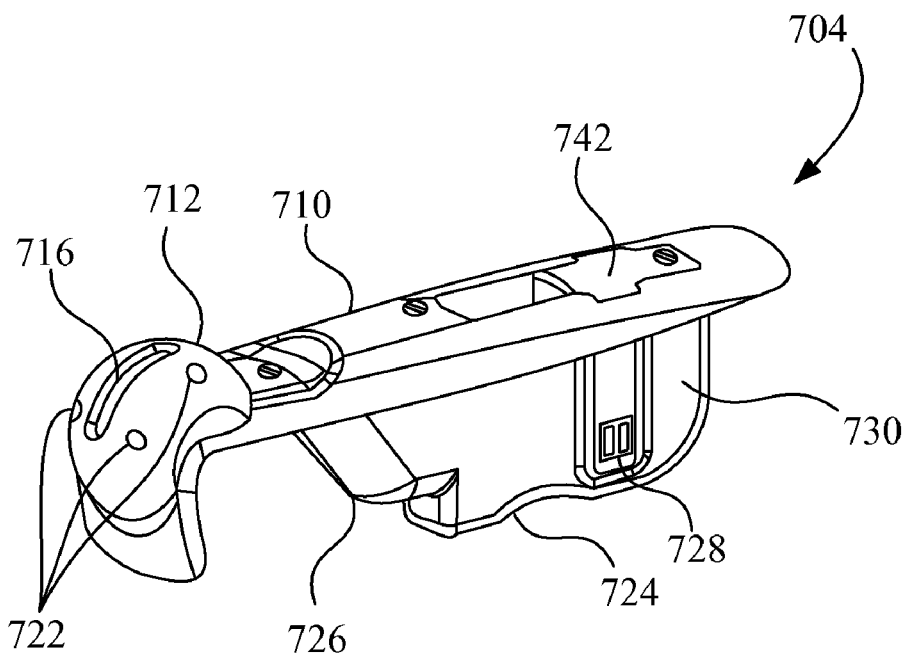
FIG. 20 is a bottom perspective view of the charging dock of FIG. 17 with the removable cover installed on the charging dock.
Figure 21A:
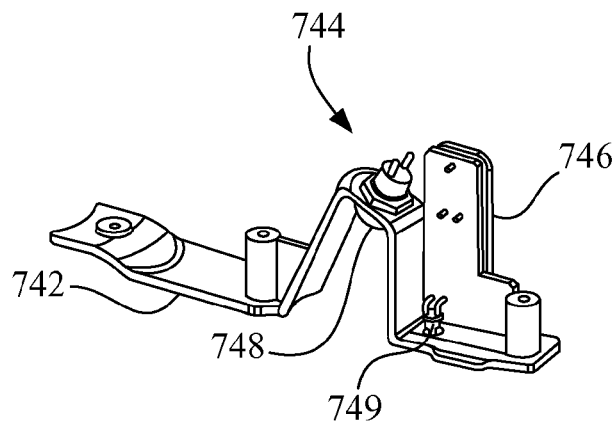
FIG. 21A is a side perspective view of the removable cover of FIG. 20 mounting the electronic components of the charging unit.
Figure 21B:
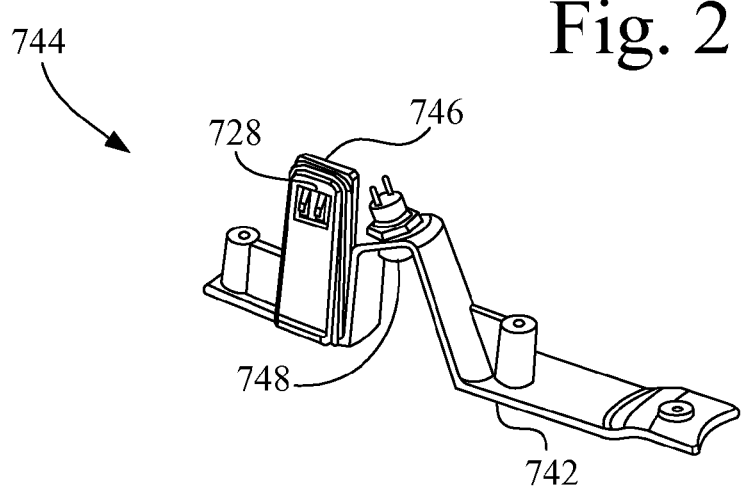
FIG. 21B is a side perspective view of the removable cover opposite to that of FIG. 21A.

Referring to FIG. 19, frame 710 has an access opening 736 leading to an internal cavity 738 of housing 724, and side wall 730 of housing 724 has an access opening 740 leading to internal cavity 738 of housing 724. Referring to FIGS. 20, 21A and 21B, a removable cover 742 is provided to cover access opening 736 of frame 710 leading to internal cavity 738 of housing 724, and a plate holding the set of electrical contacts 728 is provided to cover access opening 740. A charging unit 744 of charging dock 704 is mounted to removable cover 742.

Referring to FIGS. 21A and 21B, charging unit 744 includes a printed circuit board 746 connected in electrical communication with a power jack 748, with printed circuit board 746 mounting all electronic components of charging unit 744, such as for example, a fuse, an indicator light emitting diode (LED) 749, etc. Printed circuit board 746 includes appropriate shielding to minimize EMI interference. The terminals of power jack 748 extend upwardly through an elevated portion of removable cover 742 and are thus protected from corrosion as there is no risk of fluids (e.g. excess fluids from cleaning) being trapped on or near the terminals.

LED 749 is positioned so as not to penetrate the outer surface of removable cover 742, thus making the design more cleaner friendly. LED 749 lights up a distinct section of the plastic from within indicating that charging unit 744 is supplying correct current and that the built-in fuse is functional. If this LED stops lighting the user can see that a problem is related to charging unit 744 and not the biopsy driver assembly 12.

Printed circuit board 746 also mounts electrical contacts 728, such that electrical contacts 728 are exposed through access opening 740 of side wall 730 of housing 724 when removable cover 742 is mounted to frame 710. Also, housing 724 and removable cover 742 are configured such that all electronic components of charging unit 744 are positioned internally to housing 724 in internal cavity 738 when removable cover 742 is coupled to housing 724, i.e., when removable cover 742 is attached to frame 710.

Figure 21C:
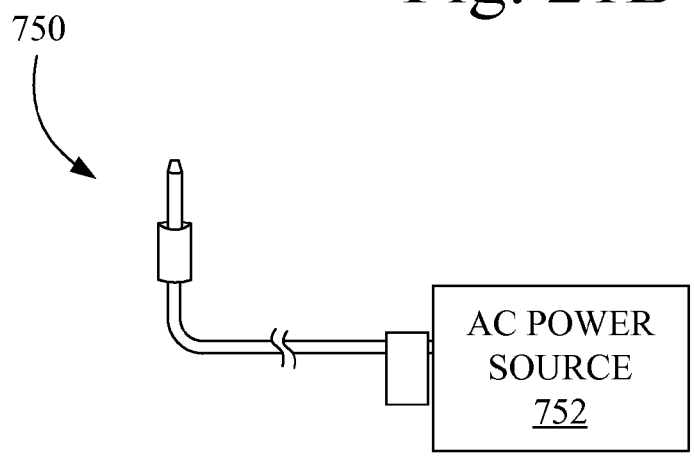
FIG. 21C is a diagrammatic representation of a power unit suitable for use with the charging unit of FIGS. 21A and 21B.

Referring also to FIG. 21C, electrical power is provided to power jack 748 via a power unit 750, which in turn is coupled to an alternating current (AC) power source 752, such as a wall electrical outlet. Power unit 750 may be configured as a transformer/rectifier unit to supply direct current (DC) power to power jack 748. As an alternative to supplying direct current (DC) current to power jack 748, those skilled in the art will recognize that power unit 750 may be configured as a transformer to supply AC current to power jack 748, with the rectifier being located on printed circuit board 746.

Figure 22:
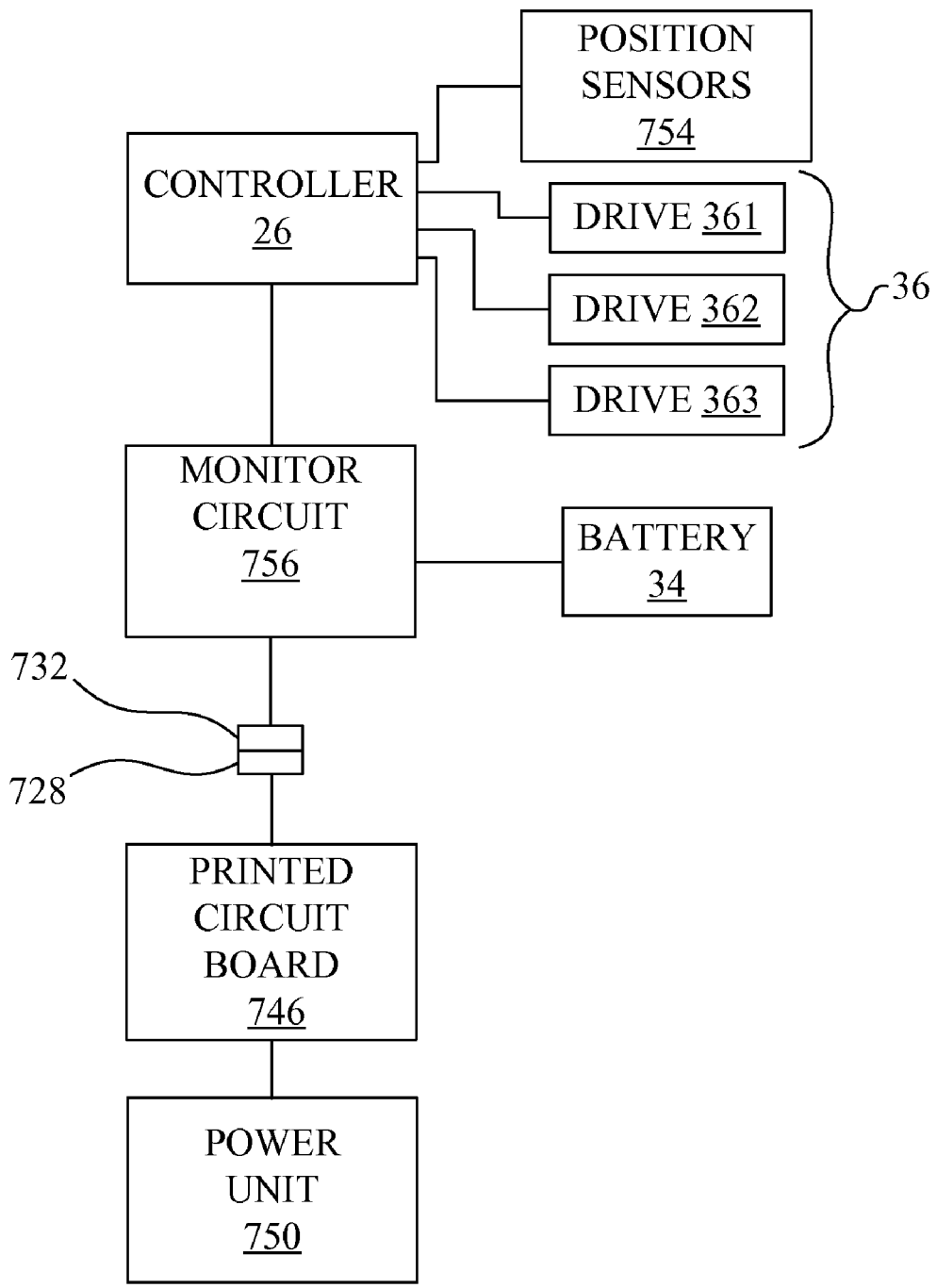
FIG. 22 is a block diagram of a control system associated with the driver assembly of FIGS. 1 and 2, and the charging station of FIG. 14.

FIG. 22 is a block diagram of a control system associated with charging station 700. As more fully described above, controller 26 is communicatively coupled to drives 361, 362, and 363. Position sensors 754 communicatively coupled to controller 26 provide feedback to controller 26 of the current positions of mechanical components of drives 361, 362, and 363. A monitor circuit 756 monitors the connection between electrical contacts 728 of charging dock 704 and electrical contacts 732 of driver assembly 12, and includes voltage and current control circuitry for facilitating the charging of battery 34. Alternatively, it is contemplated that the voltage and current control circuitry may be located in charging unit 744 of charging dock 704. Prior to mounting driver assembly 12 on charging dock 704 of charging station 700, any biopsy probe assembly 14 installed on driver assembly 12 must be removed from driver assembly 12 to vacate cavity 241 of driver assembly 12 for receiving housing 724 of charging dock 704 of charging station 700.

Figure 23:
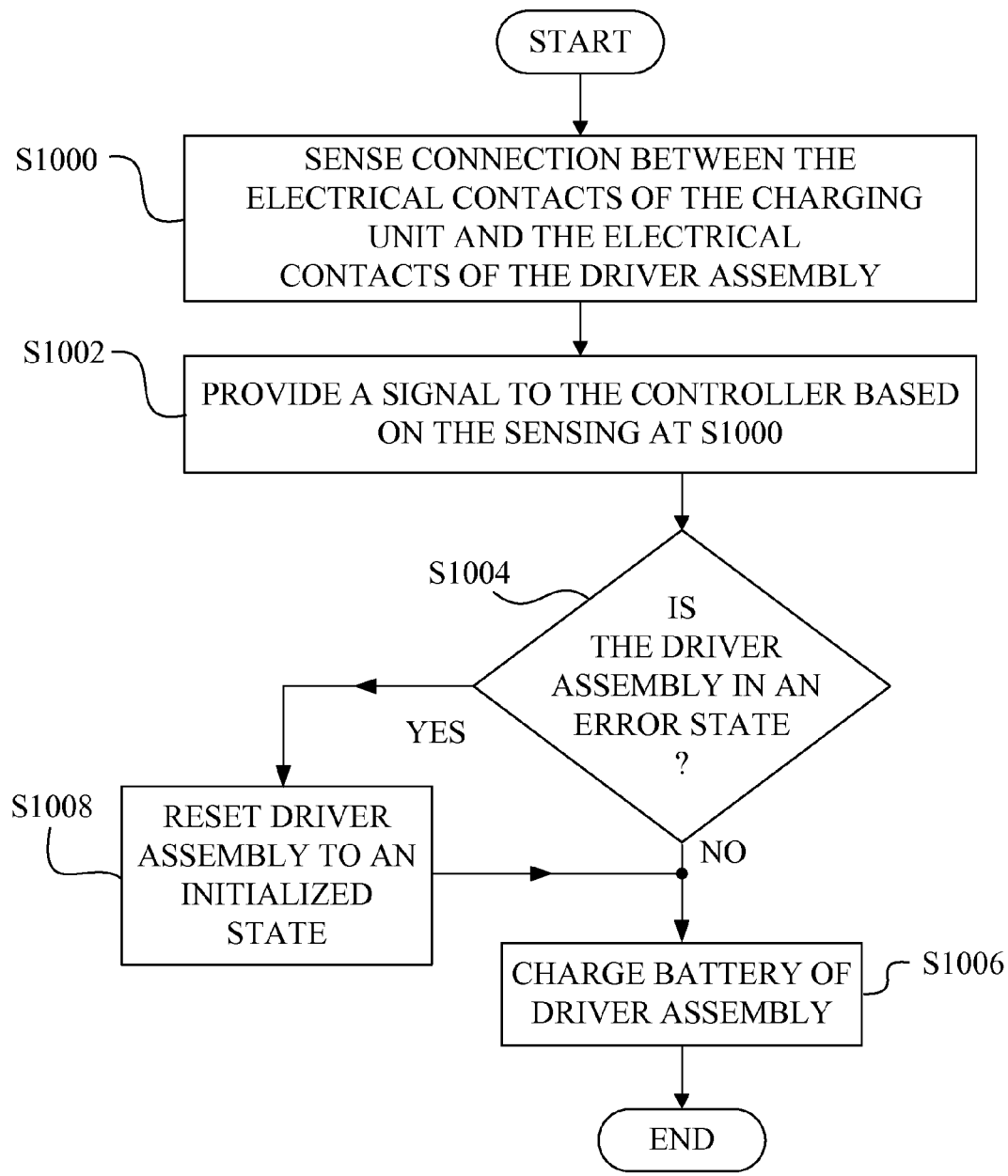
FIG. 23 is a flowchart of a method for charging a battery operated biopsy apparatus in accordance with an embodiment of the present invention.

When driver assembly 12 is mounted on charging station 700, upon connection being made between electrical contacts 728 of charging dock 704 and electrical contacts 732 of driver assembly 12, controller 26 invokes a monitor subroutine, as depicted in the flow chart of FIG. 23.

At act S1000, a connection made between electrical contacts 728 of charging unit 744 of charging station 700 and electrical contacts 732 of driver assembly 12 is sensed. For example, monitor circuit 756 may sense a connection being made between electrical contacts 728 of charging unit 744 of charging station 700 and electrical contacts 732 of driver assembly 12 by a change of voltage at electrical contacts 732.

At act S1002, based on the sensing at act S1000 a signal is provided to controller 26 of driver assembly 12 indicating that a connection between electrical contacts 728 of charging unit 744 of charging dock 704 and electrical contacts 732 of driver assembly 12 has been made. For example, charging unit 744 may provide a voltage signal, e.g., a digital "high" signal, to controller 26 via monitor circuit 756 indicating that a connection between electrical contacts 728 of charging unit 744 of charging dock 704 and electrical contacts 732 of driver assembly 12 has been made.

At act S1004, upon receiving the signal from charging unit 744, controller 26 executes program instructions to determine whether driver assembly 12 is in an error state, i.e., in a fault condition. An error state may exist, for example, if the mechanical components of one or more of drives 361, 362 and 363 are not in the proper position to facilitate a coupling of driver assembly 12 to biopsy probe assembly 14.

If no error state is present, then the process proceeds to act S1006 to begin charging battery 34.

However, if at act S1004 it is determined that an error state exists, then the process continues at act S1008 wherein controller 26 executes program instructions to reset driver assembly 12 to an initialized state. For example, controller 26 may command drives 361, 362 and 363 of electrical drive assembly 36 of electromechanical power source 28 to an initialized state. The initialized state prepositions the mechanical components of drives 361, 362 and 363 of electrical drive assembly 36 of electromechanical power source 28 to correspond to the factory preset state of a new biopsy probe assembly 14 to thereby facilitate the proper mechanical drivable coupling between driver assembly 12 and biopsy probe assembly 14.

Thereafter, the process continues to act S1006 to charge battery 34. Monitor circuit 756 of driver assembly 12 conditions the DC voltage supplied by charging dock 704, e.g., by providing voltage and current regulation, to charge battery 34.

Since no biopsy probe assembly can be installed on driver assembly 12 during recharging, by resetting driver assembly 12 at the initial stage of the charging process it is insured that driver assembly 12 is ready for drivable coupling to a new biopsy probe assembly 14 once the driver assembly 12 is removed from charging station 700.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A biopsy system, comprising:
   a driver assembly having an electromechanical power source with a battery and having a first housing configured to be grasped by a user, said first housing having a first cavity;
   a biopsy probe assembly configured for releasable attachment to said driver assembly, said biopsy probe assembly having a frame, a biopsy probe, a transmission device and a second housing, said biopsy probe and said second housing being mounted to said frame, said second housing containing at least a portion of said transmission device, said biopsy probe being drivably coupled to said transmission device, and said transmission device being configured for releasable driven coupling to said electromechanical power source of said driver assembly, said first cavity of said driver assembly being configured for receiving said second housing of said biopsy probe assembly when said driver assembly is mounted to said biopsy probe assembly, said second housing having a first shape; and
   a charging dock having a third housing and a charging unit contained in said third housing, said charging unit having a set of electrical contacts, said third housing having a second shape substantially the same as said first shape of said second housing of said biopsy probe assembly, said third housing being received in said first cavity of said driver assembly, said electrical contacts being coupled in electrical communication with said driver assembly when said driver assembly is mounted on said charging dock for charging.

2. The biopsy system of claim 1, said driver assembly further including a controller communicatively coupled to said electromechanical power source, said controller receiving a signal from said charging unit to reset said driver assembly to an initialized state when said driver assembly is mounted to said charging station.

3. The biopsy system of claim 2, wherein said reset of said driver assembly to said initialized state initializes said controller to preposition components of said electromechanical power source such that said electromechanical power source is ready to be drivably coupled to said biopsy probe assembly upon removal of said driver assembly from said charging dock.

4. The biopsy system of claim 1, said driver assembly further including a controller, said controller receiving a signal from said charging unit to reset said driver assembly to an initialized state when said driver assembly is mounted to said charging station if said driver assembly is in an error state.

5. The biopsy system of claim 1, wherein:
   said second housing is configured to contain a coiling unit of said transmission device, said biopsy probe having a sample basket arranged coaxially within a cutter cannula, with said sample basket being connected to said coiling unit; and
   said third housing of said charging dock contains all electronic components of said charging unit.

6. The biopsy system of claim 1, further comprising a removable cover to which all electronic components of said charging unit are mounted, said third housing having a second cavity such that said all electronic components are positioned internally to said third housing in said second cavity when said removable cover is coupled to said third housing.

7. The biopsy system of claim 1, wherein prior to mounting said driver assembly on said charging station, any biopsy probe assembly installed on said driver assembly must be removed from said driver assembly to vacate said first cavity in said driver assembly for receiving said third housing of said charging dock.

* * * * *